United States Patent
Dunn et al.

(10) Patent No.: US 11,615,874 B1
(45) Date of Patent: Mar. 28, 2023

(54) PERSONALIZED MEDICINE AND THERAPIES PLATFORM

(71) Applicant: VINETI INC., San Francisco, CA (US)

(72) Inventors: Jeremy Alan Dunn, Oakland, CA (US); Cathy Han, San Francisco, CA (US); Gregory George Jagiello, Tucson, AZ (US); Andrew Redoble, Concord, CA (US); Ryan Jeffrey Southwick, Pacifica, CA (US); Dan Zhang, Daly City, CA (US); Elizabeth Miriam Jones, San Jose, CA (US); Armaan Rai, San Francisco, CA (US)

(73) Assignee: VINETI INC., San Francisco, CA (US)

( * ) Notice: Subject to any disclaimer, the term of this patent is extended or adjusted under 35 U.S.C. 154(b) by 0 days.

(21) Appl. No.: 17/707,813

(22) Filed: Mar. 29, 2022

Related U.S. Application Data

(60) Provisional application No. 63/250,909, filed on Sep. 30, 2021.

(51) Int. Cl.
*G16H 20/10* (2018.01)
*G16H 10/60* (2018.01)
*G06F 8/71* (2018.01)

(52) U.S. Cl.
CPC .............. *G16H 20/10* (2018.01); *G06F 8/71* (2013.01); *G16H 10/60* (2018.01)

(58) Field of Classification Search
CPC ........... G06F 8/71; G16H 20/10; G16H 10/60
See application file for complete search history.

(56) References Cited

U.S. PATENT DOCUMENTS

| | | | |
|---|---|---|---|
| 7,581,011 B2 * | 8/2009 | Teng | H04L 63/0823 709/229 |
| 7,774,243 B1 | 8/2010 | Antony et al. | |
| 7,802,174 B2 * | 9/2010 | Teng | H04L 67/1001 715/201 |
| 8,099,758 B2 * | 1/2012 | Schaefer | H04L 63/08 726/1 |
| 10,244,965 B1 | 4/2019 | Gibson | |

(Continued)

FOREIGN PATENT DOCUMENTS

| | | |
|---|---|---|
| WO | 2001024771 A1 | 4/2001 |
| WO | 2012099973 A2 | 7/2012 |

(Continued)

OTHER PUBLICATIONS

Levine et al., "Global Manufacturing of CAR T Cell Therapy," Molecular Therapy: Methods & Clinical Development vol. 4 Mar. 2017, pp. 92-101.

(Continued)

*Primary Examiner* — Douglas M Slachta
(74) *Attorney, Agent, or Firm* — Perkins Coie LLP

(57) ABSTRACT

Disclosed are devices, systems, methods, and computer program products for managing the development and treatment supply chain in delivering personalized medicine therapies. In some aspects, a unified configuration system (UCS) for an enterprise software platform is described that enables and facilitates individual stakeholders of the personalized medicine development and treatment supply chain to create and manage independent configurations of their supply chain management software for an enterprise software platform.

18 Claims, 20 Drawing Sheets

(56) References Cited

U.S. PATENT DOCUMENTS

| | | | |
|---|---|---|---|
| 10,817,949 B1 | 10/2020 | Wieduwilt et al. | |
| 10,853,039 B2* | 12/2020 | Patel | G06F 8/10 |
| 2002/0187526 A1 | 12/2002 | Ruben et al. | |
| 2006/0172422 A1 | 8/2006 | Dzekunov et al. | |
| 2006/0179058 A1* | 8/2006 | Bram | G06F 21/629 707/999.009 |
| 2010/0235813 A1* | 9/2010 | Manczak | G06F 8/71 717/121 |
| 2011/0119290 A1* | 5/2011 | Dhoble | G16H 80/00 707/769 |
| 2012/0077546 A1* | 3/2012 | Kawa | H04W 4/50 455/566 |
| 2012/0101847 A1* | 4/2012 | Johnson | G16H 10/60 705/2 |
| 2012/0198218 A1* | 8/2012 | Tukol | G06F 8/658 713/1 |
| 2013/0074158 A1* | 3/2013 | Koskimies | H04L 63/0428 726/4 |
| 2013/0212132 A1* | 8/2013 | Rogers | G06F 16/9535 707/803 |
| 2014/0136259 A1 | 5/2014 | Kinsey, II et al. | |
| 2016/0267247 A1* | 9/2016 | High | G16H 20/10 |
| 2017/0039330 A1 | 2/2017 | Tanner, Jr. et al. | |
| 2017/0212729 A1* | 7/2017 | Sridhar | G06F 8/60 |
| 2017/0364637 A1 | 12/2017 | Kshepakaran et al. | |
| 2018/0096175 A1 | 4/2018 | Schmeling et al. | |
| 2018/0264347 A1 | 9/2018 | Tran et al. | |
| 2019/0088373 A1 | 3/2019 | Sarmentero | |
| 2019/0096534 A1 | 3/2019 | Joao | |
| 2019/0214119 A1 | 7/2019 | Wachira et al. | |
| 2020/0058381 A1 | 2/2020 | Patel | |
| 2020/0167725 A1 | 5/2020 | Bolene et al. | |
| 2020/0177386 A1 | 6/2020 | Mahmood et al. | |
| 2020/0219605 A1* | 7/2020 | Govindjee | G16H 40/67 |
| 2020/0364588 A1 | 11/2020 | Knox | |
| 2020/0372990 A1* | 11/2020 | Ho | A61B 5/742 |
| 2021/0110897 A1 | 4/2021 | Ginsburg et al. | |
| 2021/0280287 A1 | 9/2021 | Mahmood et al. | |
| 2022/0019446 A1* | 1/2022 | Maloney | G06F 8/65 |

FOREIGN PATENT DOCUMENTS

| | | |
|---|---|---|
| WO | 2015142675 A2 | 9/2015 |
| WO | 2017079703 A1 | 5/2017 |
| WO | 2017096327 A2 | 6/2017 |
| WO | 2017117112 A1 | 7/2017 |
| WO | 2018187332 A1 | 10/2018 |
| WO | 2019055896 A1 | 3/2019 |

OTHER PUBLICATIONS

Olweus J. (2017). Manufacture of CAR-T cells in the body. Nature biotechnology, 35(6), pp. 520-521. https://doi.org/10.1038/nbt.3898.

Merhavi-Shoham et al., "Adoptive Cell Therapy for Metastatic Melanoma," The Cancer Journal, vol. 23, No. 1, Jan./Feb. 2017, pp. 48-53.

Kochenderfer et al., "Lymphoma Remissions Caused by Anti-CD19 Chimeric Antigen Receptor T Cells Are Associated With High Serum Interleukin-15 Levels," J Clin Oncol. Jun. 1, 2017;35(16):1803-1813. doi: 10.1200/JCO.2016.71.3024. Epub Mar. 14, 2017. PMID: 28291388; PMCID: PMC5455597.

Vineti Inc., Product Data Sheet, www.vineti.com, 2021, 2 pages.

Vineti, Inc., "Cell and Gene Therapy, Supply Chain Management: Readiness Checklist," 2021, 4 pages.

Vineti, Inc., "Chain of Identify (COI) Identifier, An industry standard recommendation for personalized therapeutics, As presented to the Standards Coordinating Body for Regenerative Medicine," Oct. 2020, 15 pages.

Vineti, Inc., "Personalized Supply Chain Strategies, A Supply Chain Readiness Guide for cell therapies, gene therapies, and personalized cancer vaccines," 2020, 22 pages.

PCT/US2019/63747—International Search Report dated Mar. 10, 2020, 2 pages.

International Patent Application No. PCT/US2022/075785—International Search Report and Written Opinion, dated Sep. 29, 2022, 12 pages.

\* cited by examiner

PERSONALIZED MEDICINE AND THERAPIES PLATFORM

CROSS-REFERENCE TO RELATED APPLICATION(S)

This patent document claims priority to and the benefit of U.S. Provisional Patent Application No. 63/250,909, filed Sep. 30, 2021, and is incorporated herein by reference in its entirety.

TECHNICAL FIELD

The present disclosure is directed to systems, methods, devices, and computer program products for managing the development and treatment supply chain in delivering personalized medicine therapies.

BACKGROUND

Personalized medicine is a medical treatment model that provides medical decisions, practices, therapies, interventions and/or products specifically tailored to an individual patient based on the individual's predicted response or risk of disease. Immunotherapy is a form of personalized medicine rapidly emerging for disease treatment and prevention. Immunotherapy includes, for example, engineering a modified version of a patient's own biological material (e.g., immune cells) and reintroducing the engineered biological material into the patient to initiate and/or supplement the patient's immune response to combat a disease. For example, CAR T-cell therapy is a cancer treatment that involves the extraction of T-cells from a patient's blood and modifying the cell surface to include chimeric antigen receptors that facilitate the production of a chemical to attack tumor cells. These and other individualized approaches allow for the provisioning of customized therapies based on calculated predictions for how treatments may work best for a particular patient.

Although these treatments are revolutionizing disease treatment, a complex chain of processes must be undertaken in order to process, generate, and deliver the therapeutics ultimately administered to the patient. Personalized medicine supply chains are fraught with logistical challenges, scheduling challenges, stakeholder coordination challenges, monitoring and tracking challenges, and other related problems that impede the ability to implement personalized medicine on a large or global scale.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure. The drawings should not be taken to limit the disclosure to the specific embodiments depicted, but are for explanation and understanding only.

DETAILED DESCRIPTION

Figure 1A:
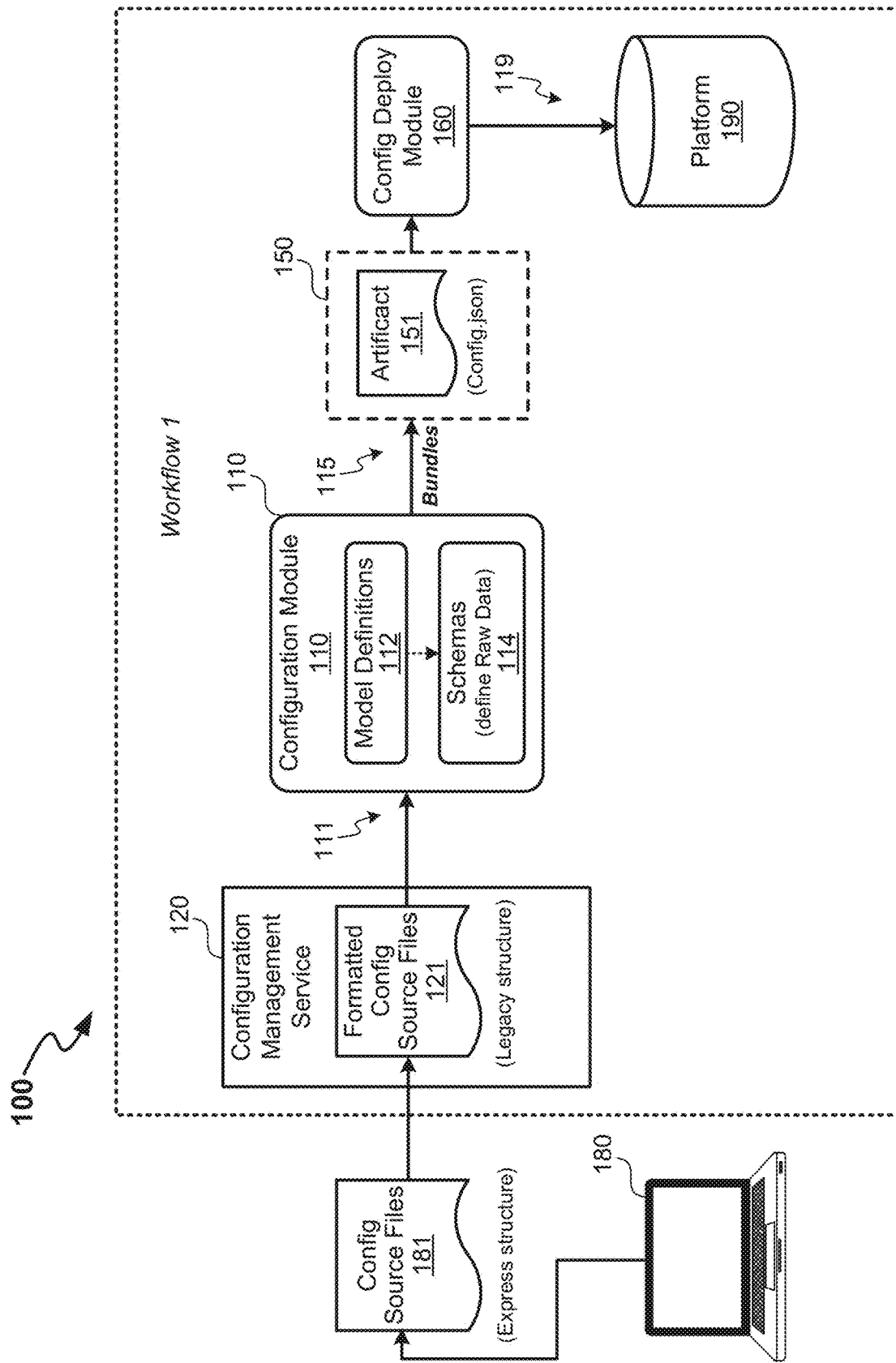
FIG. 1A shows a diagram depicting an example embodiment of a unified configuration system for managing a client configuration of enterprise software configured in accordance with some implementations of the present technology.

The present disclosure is directed to systems, devices, methods, and computer program products for providing a unified configuration system (UCS) that includes one or more workflow engines for an enterprise software platform (particularly, for an enterprise software platform designed to orchestrate a personalized medicine treatment (e.g., CAR T-cell therapy) among multiple stakeholders) and that enables and facilitates a client device operating its software application version of the enterprise software platform to introduce new functional features for the software application without introducing a code change to the enterprise software platform. Further, in some implementations described in further detail below, the disclosed technology can be used to build, manage, and facilitate a data configuration service for an enterprise software platform.

In the implementations described below, the UCS including one or more workflow engines for an enterprise software platform is primarily described in the context of personalized medicine treatment (CAR T-cell therapy). It will be appreciated, however, that the disclosed technology can be utilized with a variety of other cell and gene therapies, personalized medicine treatments, as well as a variety of other medical or non-medical systems. Furthermore, a person skilled in the relevant art will understand (i) that the technology may have additional implementations than illustrated in FIGS. 1A-10 and (ii) that the technology may be practiced without several of the details of the implementations described below with reference to FIGS. 1A-10.

Overview

Advanced therapies, particularly personalized therapies, have forced a paradigm shift in medical supply chain management. Instead of coordinating several components for large batches of 'one-size-fits all' therapies, such as vaccines, blockbuster drugs, etc., pharmaceutical manufacturers and health care professionals must now manage a highly complex supply chain of personalized components for production of an individualized therapy in very small batches—sometimes as small as one therapy per patient—and at growing volumes.

Presently, supply chains for personalized therapies such as CAR T-cell therapy are distributed in a manner built around patients and donors, but must also account for activities and constraints associated with the other supply chain stakeholders, particularly (i) manufacturers of biological material, (ii) transporters of materials, and (iii) health care providers (HCPs) and their settings, including hospitals, laboratories, and clinics. As such, supply chains are highly complex structures to view, track, and manage for each supply chain stakeholder, particularly in real time. For example, obstacles exist for accurate and efficient accounting of the chain-of-identity (COI) and chain-of-custody (COC) of materials to ensure the safety of the end personalized therapy product across the entire product cycle from "vein to vein," i.e., from the earliest event such as extraction of biological material from a patient for creating the personalized therapy to a last event such as delivery of the personalized therapy for treating the patient's disease or condition.

In the "vein to vein" lifecycle to develop and deploy a personalized therapy, there are dozens, if not hundreds, of stakeholder handoffs that must be enabled, tracked, and documented for every patient product. Each product journey, i.e., the transition of a material or materials from one stakeholder or process to another, is likely to be highly variable and susceptible to schedule changes and unexpected events that can disrupt supply chain flow, and thereby devastate the personalized therapy for a patient. For example, presently, it is very difficult to align the starting material collections process with manufacturing capacity such that precious cellar material is not lost and manufacturing capacity is utilized and not overbooked or over extended. Also, when a disruption in the supply chain occurs, the supply chain must be able to adapt to unexpected events; however, the ability to reschedule events is not feasible without integrated tools with connected data flows and orchestration, particularly orchestration of the entire supply chain—including logistics—from order to treatment, with a single source of real-time transparency and visibility.

One approach aimed to address these and other challenges to meet the demands for personalized medicine is a cloud-based, individualized medicine software platform technology, developed by Vineti, Inc., the assignee of the present technology. Vineti's platform technology is an aPaaS (Application Platform as a Service), which is a purpose-built enterprise software service providing a common technological foundation to meet each individual client needs through end-user administrator configuration, and not by creating standalone custom builds. Aspects of the platform technology are discussed in U.S. Patent Publication No. 2020/0177386A1, which is incorporated by reference in its entirety as part of the disclosure of this patent document. For example, the exemplary cloud-based platform technology executes a range of operations related to data communications and transactions to coordinate events that occur in an individualized medicine supply chain, e.g., including but not limited to ordering and scheduling of biological material extraction, material and/or kit delivery, material and/or kit tracking, automated courier scheduling, intermediary and final product preparation, capacity and resource management, etc. In some aspects, the exemplary cloud-based platform technology is able to facilitate interactions between an individualized medicine system and one or more nodes of a blockchain configured to store event data and identification data corresponding to transactions that occur along an individualized medicine supply chain.

Traditionally, pharmaceutical manufacturers or HCPs manage their roles in the practice of generalized medicine using custom software. Yet, as personalized medicine continues to grow, custom software architecture has become incapable to facilitate personalized medicine treatment practices and address, let alone satisfy, supply chain stakeholder needs. As such, enterprise software has become a more practical model to build a personalized medicine supply chain. The above-referenced platform technology is one example of an enterprise software platform developed for personalized medicine management.

Generally, enterprise software is a collection of computer programs that have common applications (e.g., business- or commerce-focused), modeling tools for managing how an organization works, and development tools for building applications unique to the organization. Enterprise software is architected for addressing large-scale problems across an 'enterprise' (multiple stakeholders in a community, for example), rather than an individualized or single-entity problem, for the sake of improving the enterprise's productivity and efficiency through software- and network-based support functionality. As such, distinctive features for individual end-users of enterprise software are difficult to create and manage. In contrast, custom software is software that is specially developed for a particular or individualized organization or user, i.e., it is designed to meet the customer's particular, individualized preferences and expectations.

An end-user ("client" or "tenant") of a software application for an enterprise software platform will have their own unique needs for their version of the software application. Thus, enterprise software providers typically develop the enterprise software platform that allows for individualized configurations associated with the individual client's software application. However, providing individualized configurations for clients conventionally requires the enterprise software provider (and in some instances, the client itself) to create and manage specific code for the enterprise software platform in order to configure the client's application to have and execute the different functionalities and/or appearance for each client's desired configuration. This creates challenges in balancing the flexibility of how configurable the enterprise software may be, i.e., the more inflexible the configuration process, the easier it is for enterprise software providers to manage the individual client configurations, but the client's software application may be less useful in satisfying each clients' needs; and the more flexible the configuration process, the more complex it is for enterprise software providers to manage the individual client configurations, but the client's software application is more valuable and adept to satisfy their needs.

As such, a primary challenge in developing and providing an enterprise software platform is balancing how much flexibility to allow for client configurations to their software. And when at least some flexibility is to be built into the platform, another key challenge is creating a configuration process for clients to configure certain features and functionalities of their software that serve their needs without over-burdening the clients with complex configuration rules, protocols, and interfaces. And yet further, if more client-side configuration flexibility could be afforded, then additional challenges arise for how the platform can allow multiple and efficient configurations to the client's version of the software application of the enterprise software platform, so as to serve their ever-changing needs.

Conventional means for configuring software in an enterprise software platform typically require the enterprise software provider to develop custom configurations (e.g., lines of code) for each client/customer of the platform (e.g., which may be based on specifications or configuration files from the client). This ultimately results in substantial time and cost to the provider (and in some instances, the client) and requires expertise on behalf of the enterprise software provider to produce lots of configuration files for each customer. For example, developing these separate configuration files typically involves coding sequential process steps (e.g., often having multiple conditions in a step) that the end user would carry out as the end user implements the application, including coding what functionalities are available to implement in each step. Therefore, the present, conventional practice for end user enterprise software configuration is inefficient and cumbersome, both to the client enterprise software users and the enterprise software providers. What is needed is a system that can receive each individual client's desired configuration specifications and efficiently transform the enterprise software platform in a unified manner from a plurality of disparate client configurations for their respective software application.

The present technology is directed to devices, systems, methods, and computer program products for providing a unified configuration system (UCS) that includes one or more workflow engines for an enterprise software platform (particularly, for an enterprise software platform designed to orchestrate a personalized medicine treatment among multiple stakeholders) and that enables and facilitates a client device operating its software application version of the enterprise software platform to introduce new functional features for the software application without introducing a code change to the enterprise software platform.

In example embodiments, the UCS provides a set of workflows, data structures, and user interfaces that create features for an enterprise software platform (including Application Platform as a Service (APAAS) systems) that enables client computers to configure their version of the enterprise software, by text-based and/or visual-object-based configuration, without writing new programs to integrate into the software (e.g., no software updates). For example, in some implementations, the UCS can include a plurality of modules that regulate one or more operations of the UCS, e.g., including a configuration review process (that allows a user to review and confirm proposed configuration changes prior to persisting them in the software platform), providing pre-configured standard components to facilitate a client configuration implementation, and a configuration assistant to guide a configuration administrator in a configuration implementation, e.g., which for a personalized medicine enterprise software platform can ensure best practices for patient safety. These and other exemplary tooling of the UCS can provide unique advantages to an enterprise software platform, e.g., including but not limited to (i) acceleration of controlled testing for compliance teams; (ii) configuration data validation framework that supports back-end and UI; (iii) application data import/export functionality; (iv) form-like UI configurations and previews (for design review) for form-based configurations to the platform; (v) unified workflow and scheduling configuration tooling; and (vi) self-service deployment of configuration and self-service identity provider (IdP) management (e.g., which can enable support for single HCP account).

In some embodiments of the UCS, the system provides development tooling that can be rendered via a text-based user interface (TUI) and/or a graphical user interface (GUI) to accommodate a variety of different users of varying programming levels, e.g., including both non-technical users and highly experienced developers. For example, in some implementations, the UCS includes a TUI providing a developer-like workflow for technical users.

Further advantages of the disclosed embodiments of the UCS include enabling client computers operating the enterprise software platform to configure and create changes in the software through a specialized UI, e.g., from configuration creation to configuration deployment to controlled environments and production. In some implementations of the UCS for personalized therapy management enterprise software, for example, the UI allows the end user administrator to (i) edit business process model and notation (BPMN) software inside config tooling, e.g., by providing a process skeleton BPMN to enable scheduling optimization and rescheduling across entire supply chain; (ii) create and manage products and branding, e.g., which can be valuable for certain end users such as a pharmaceutical manufacturer of any size; (iii) define custom fields, create object state transitions, and connect schema to UI pages and integrations, e.g., via object model UI; (iv) incorporate pre-built best practices components; and (v) provide automatic config recommendations.

Unified Configuration System (UCS)

For enterprise software platforms, client-side (end user) configurations are typically managed by the enterprise software provider as individual repositories, where the enterprise software provider will regulate each configuration through version-control and utilizing third party workflow engines and management tools, such as GITHUB®. A workflow engine is a form of software that helps to manage complex processes (e.g., business activities) that provide materials or services and/or process information. A workflow engine typically uses a database server to organize and track an implementation of a workflow (i.e., a workflow is a series of orchestrated and repeatable tasks that are designed to accomplish a goal or goals of the organization, such as a business).

FIG. 1A shows a diagram depicting an example embodiment of a unified configuration system (UCS) 100 configured in accordance with the present technology. The UCS 100 is a software architecture, which is part of and/or integratable with an enterprise software platform, for managing a client-initiated configuration of the client's version of the enterprise software application, implementable on client computer(s) operating the client's enterprise software and platform provider computer(s) (e.g., servers and database-hosting computers).

In example embodiments, the UCS 100 includes a computer program product stored on one or more non-transitory, computer-readable medium(s) and having instructions (code) that, when executed by one or more processor(s) of one or more computing device(s) (e.g., servers), cause the computing device(s) to perform operations according to the instructions. In some embodiments, the software architecture of the UCS 100 is resident on one or more servers that execute instructions across a plurality of computing devices (e.g., server(s), client(s), database(s), etc.) in communication with each other over a network, such as the "cloud." The diagram of FIG. 1A illustrates an example for client software configuration managed by the UCS 100 where the UCS 100 receives a set of configuration source files from a client computer 180; formats, processes and validates the configuration source data; and deploys and persists the client configuration for the enterprise software platform 190.

In some example embodiments like that shown in FIG. 1A, the UCS 100 includes a configuration module 110 that is configured with a set of data processing tools (e.g., algorithms) to generate and deploy a bundled set of configuration files 151 (also referred to as artifact 151) based on processing of configuration source files received from a source, thereby creating a validated configuration data set. The configuration module 110 provides a data configuration service to produce a validated, bundled configuration data set (i.e., artifact 151, e.g., stored in a memory 150); such that within the data configuration service exists a set of schemas that define the raw data 114 that the configuration module 110 addresses for production of the artifact 151. The UCS 100 includes a configuration deployment module 160 that provides a deployment service, where the validated configuration data set is persisted to the enterprise software platform 190. The enterprise software platform (e.g., illustrated in FIG. 1A as a database) can be stored and implemented by computer(s) in the cloud. In some implementations, for example, the data configuration service implemented by the configuration module 110 is accessible to a user via an internal command line interface (CLI); whereas in some implementations, for example, the data configuration service is accessible to a user via a GUI.

The set of configuration source files may be received at the configuration module 110 directly from a data management module to provide a configuration management service (CMS) 120, where the received configuration source files are in the form of a formatted set of configuration source files 121. In some implementations, for example, the received configuration source files are formatted in a legacy file structure associated with the format of the enterprise software platform. In some implementations, like that shown in FIG. 1A, the CMS 120 receives a client-generated set of configuration source files 181 (e.g., such as express configuration source files provided by a client in a format associated with the client's software application version of the enterprise software platform), which the CMS 120 is configured to process in order to create the formatted configuration source file 121. During operation, for example, the CMS 120 determines the correct interface to deliver the configuration for the client based on the type of configuration that it was provided. The CMS 120 processes the received set of configuration source files 121 by subdividing and orchestrating the parsed data based on the configuration that was uploaded and the pathways available in the UCS 100.

In some embodiments of the UCS 100 like that shown in FIG. 1A, for example, the UCS 100 includes a single configuration pathway, also referred to as "Workflow 1" that includes processes 111, 115, and 119, which is the workflow for the application configuration that impacts the way the client version of the enterprise software application will operate. In some embodiments of the UCS 100 like that shown in FIG. 1B (discussed later), for example, the UCS 100 includes two major configuration pathways: Workflow 1 and a "Workflow 2" that includes processes 113 and 117, which is the workflow for the data, which includes the software application's permissions, roles, users, and fixtures. In such example embodiments, the configuration module 110 can process and manage the application configuration workflow for Workflow 1 (beginning at process 111 discussed below), and the data configuration workflow(s) for Workflow 2 can be processed and managed separately from the configuration module 110 by a data configuration module 130 of the UCS 100 (beginning at process 113, discussed later). It is noted that, in some alternative example embodiments of the UCS 100), both of the application configuration workflow and the data configuration workflow(s) can be managed in one or more workflows implemented by the configuration module 110.

Referring to FIG. 1A, in some implementations of the UCS 100 for an exemplary workflow (Workflow 1), for example, the configuration module 110 can read in (at a process 111) a set of formatted configuration source files 121, upon which the configuration module 110 applies a configuration model 112 to validate the set of source files and subsequently build the validated, bundled set of configuration source files (at process 115) into an artifact 151 (also referred to as "Config.json"), e.g., constituting a bundled configuration data set. The configuration model 112 (also referred to as "Model Definitions") include a schema that defines the structure and validity of the config data that is received, such that the configuration module 110 processes the configuration source data (e.g., formatted configuration source file 121) to produce validated configuration source data. In some implementations, for example, the configuration module 110 bundles the validated set of configuration source files to produce the artifact 151 (Config.json). In these examples, Config.json is a baseline software-development artifact that is to be processed by a UCS deployment service to be persisted into the platform database. The Workflow 1 can conclude at the process 119 where the validated configuration data set is persisted to the enterprise software platform 190 by the configuration deployment module 160.

Figure 1B:
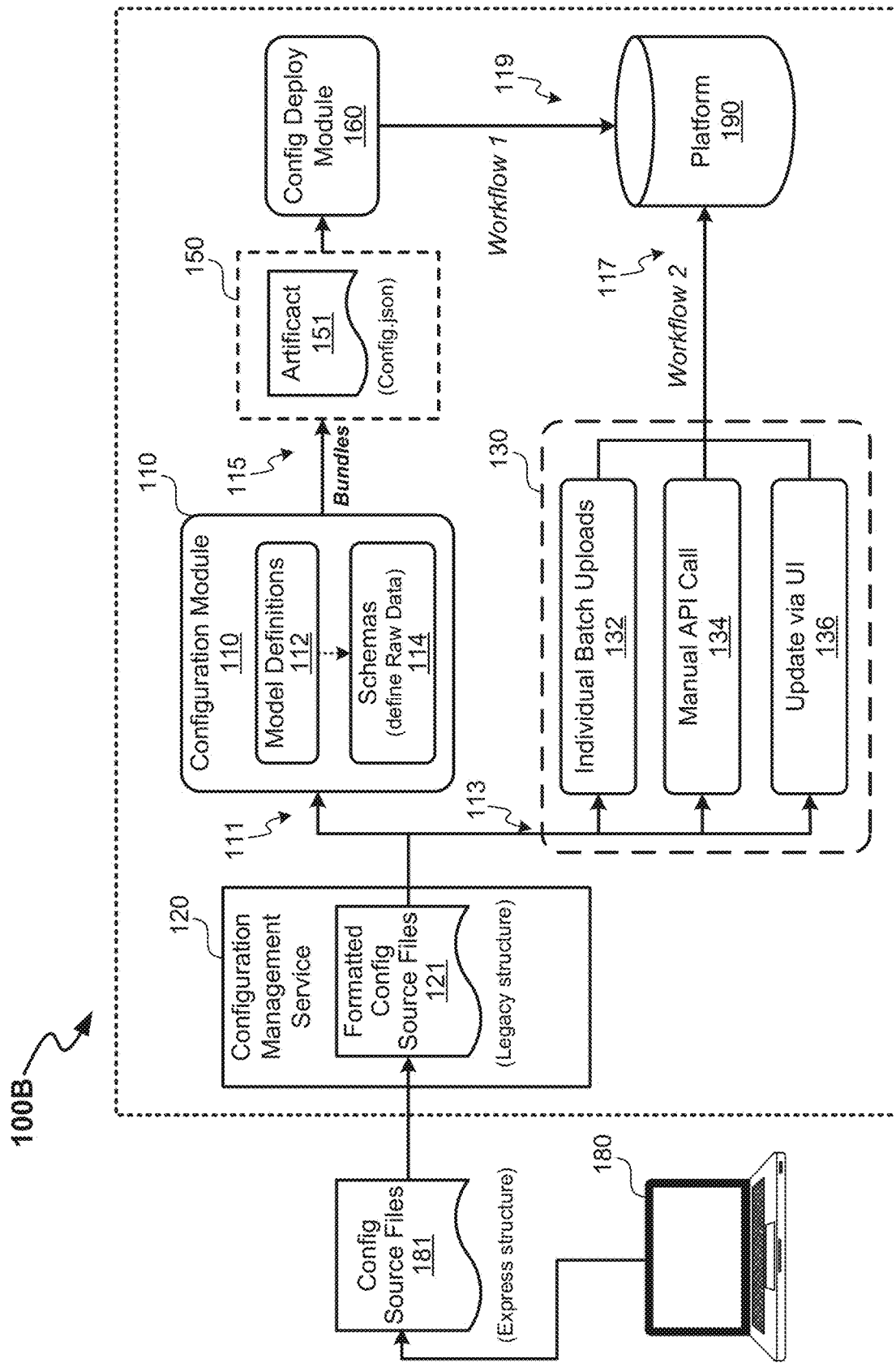
FIG. 1B shows a diagram depicting another example embodiment of a unified configuration system for managing a client configuration of enterprise software configured in accordance with some implementations of the present technology.

FIG. 1B shows a diagram depicting another example embodiment of the UCS 100, referenced in FIG. 1B as UCS 100B, that is configured in accordance with the present technology. The UCS 100B is configured to implement Workflow 1 and Workflow 2, e.g., whether in parallel, sequentially in any order, or a combination of parallel and sequentially.

In some implementations of the UCS 100B, for example, the set of formatted configuration source files 121 can be apportioned to be handled by one or more workflows (designated as Workflow 2), which can be separate from the example Workflow 1 that is managed by the configuration module 110. For example, in this example Workflow 2, services of the data configuration module 130 including a hatch upload module 132 (also referred to as "Individual Batch Uploads"), an API call module 134 (also referred to as "Manual API Call"), and an update module 136 (also referred to as "Update via UI") can be used to manage (e.g., update) permissions, roles, users, and/or fixtures in accordance with the configuration of the client's version of the application that is managed by the configuration module 110. In such implementations of the Workflow 2 by the UCS 100B, for example, the services of the data configuration module 130 configure the client configuration data at the process 113 and persist the client configuration data to the enterprise software platform 190 at the process 117.

In some implementations, for example, these additional modules, i.e., the batch upload module 132, the API call module 134, and/or the update module 136, can be accessed individually via a command line interface (e.g., internal command line associated with the platform 190), or via postman, or via a cURL command. These additional modules can manage a portion of configuration management that is outside the purview of the configuration module 110, e.g., where the configuration module 110 handles the processing and deployment of a portion of the client configuration source data, and one or more of the additional modules 132, 134, and/or 136 handle direct deployment of the remaining portion of the client configuration source data. One example of a direct deployment, in which certain configuration source data is received, managed, and deployed by one or more of the additional modules 132, 134, and/or 136, includes certain data objects like roles, permissions, or site data, which can achieve the main goal of getting that version of the client's configuration persisted in a single tenant's instance for the enterprise software platform 190.

One of the challenges in operating a configuration source file management service is balancing the need for flexibility in the client's configuration with the strictness of the configuration source file structures that are to be processed, persisted, and deployed. As an illustrative example, in a personalized therapy software platform, a pharmaceutical drug maker may have a drugs or therapeutic substance managed in the platform (for personalized therapy, including CAR T-cell therapy), in which the drug has two separate production lines (e.g., one in U.S. and one in Europe). The client administrator may want to make a change to one or both separate production lines and update to the platform, and therefore may choose to write each client configuration source data for those production lines as separate instances of configuration because, for the client, it is easier to parallelize the development and keep specific changes in one production line isolated from another. Whereas, for the software platform (like the example shown in FIGS. 1A and 1B), the client's configuration changes become merged into one personalized therapy object, e.g., as part of a large artifact (e.g., Config.json). Therefore, the intake of the configuration source file(s) from the client, e.g., at CMS 120, provides for flexibility and intelligent parsing, translation, and/or assignment of aspects of the client configuration source data to format the configuration source file(s) for the configuration module 110 to subsequently process. For example, the CMS 120 can include a plurality of compilation tools that each correspond to different formats and/or syntax for express structure of the client configuration source file(s) 181. Notably, the different forms of express structure do not impact the platform 190, since the configuration module 110 is devised to create a single (large) artifact 151 (e.g., Config.json).

Yet, the example architecture of the UCS 100 and 100B shown in FIG. 1A and FIG. 1B, respectively, include some aspects that other embodiments of the UCS disclosed herein address. For example, the configuration module 100 of the UCS 100 embeds the validation schemas ("Model Definitions") in the module 100, which can add some complexity to developments of new configuration features of the UCS 100. Also, in the example UCS 100 shown in FIG. 1A, the configuration module 100 is to receive a specific file structure of the formatted configuration source file(s) 121, formatted by the CMS 120, which can involve translation services that sometimes may require intervention by a user of the enterprise software platform.

Figure 2A:
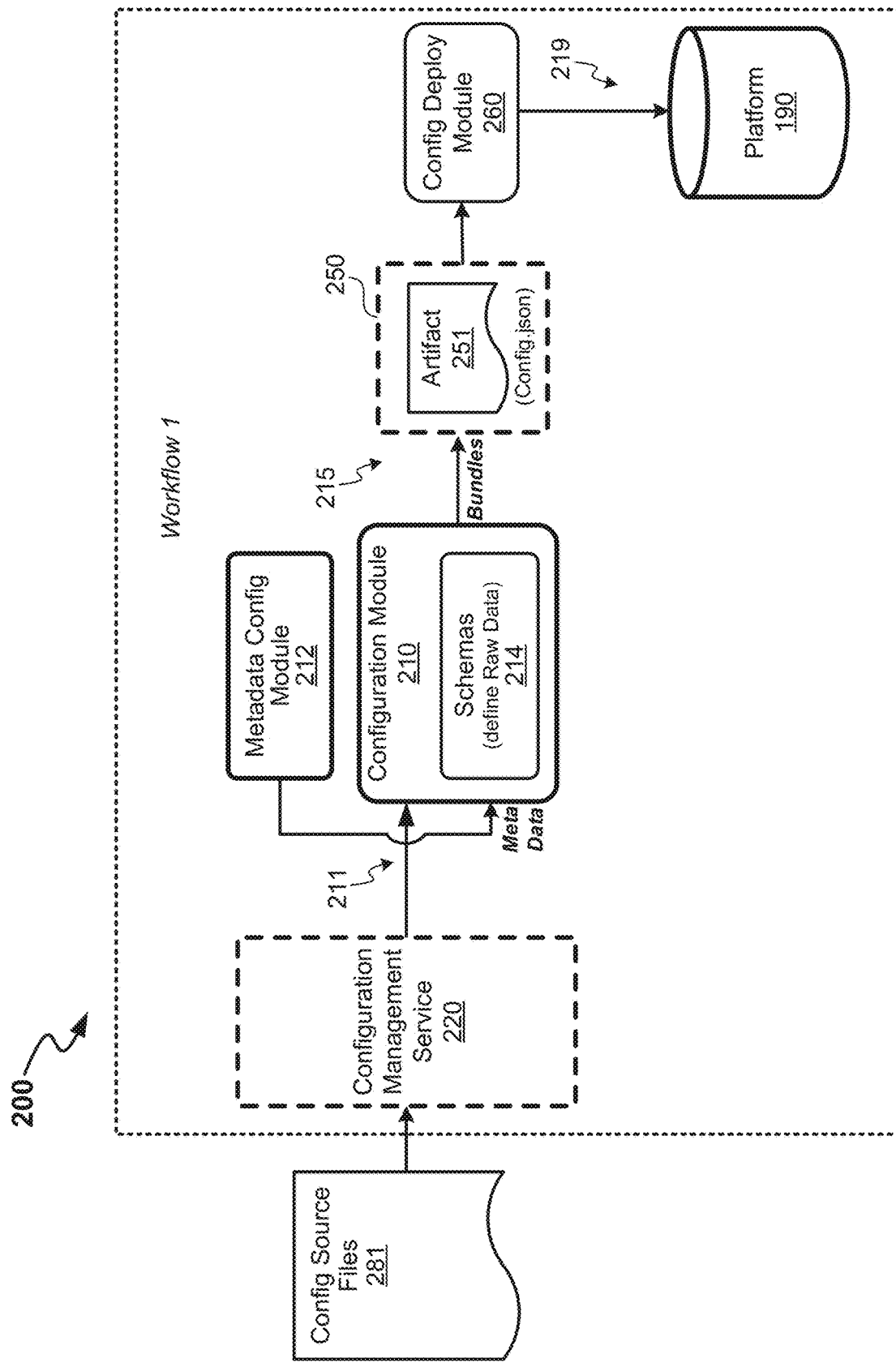
FIG. 2A shows a diagram depicting another example embodiment of a unified configuration system for managing a client configuration of enterprise software configured in accordance with some implementations of the present technology.

FIG. 2A shows a diagram depicting another example embodiment of a UCS 200 for managing a client configuration of enterprise software configured in accordance with the present technology. In some example embodiments like that shown in FIG. 2A, the UCS 200 includes a configuration module 210 to generate and deploy a bundled set of configuration files 151 (also referred to as artifact 251) based on configuration source files received from a source, creating a validated configuration data set (i.e., artifact 251, e.g., stored in a memory 250). The configuration module 210 includes a configuration build tool that provides a data configuration service, in which the configuration build tool parses and validates the received configuration source files using configuration model definitions provided by a configuration module 210 of the UCS 200 to serialize and build a configuration bundle, i.e., the artifact 251, e.g., in the form of Config.json. The configuration module 210 includes a set of schemas 214 that define raw data that the configuration module 210 addresses based on metadata provided (via the metadata configuration module 212) for production of the artifact 251. The UCS 200 includes a configuration deployment module 260 that persists the validated bundled configuration data set to the enterprise software platform 190, e.g., in a database of the platform 190.

Similar to the embodiment shown in FIG. 1A, in some embodiments of the UCS 200 (like that shown in FIG. 2A), for example, the UCS 200 includes a single configuration pathway, also referred to as "Workflow 1" that includes processes 211, 215, and 219, which is the workflow for the application configuration that impacts the way the client version of the enterprise software application will operate. In some embodiments of the UCS 200 like that shown in FIG. 2B (discussed later), for example, the UCS 200 can include two major configuration pathways: Workflow 1 and a "Workflow 2" that includes processes 213 and 217, which is the workflow for the data, which includes the software application's permissions, roles, users, and fixtures.

In implementations, the configuration module 210 receives input configuration source files (at a process 211) for building a client-specified configuration of the client's version of the enterprise software application. In some embodiments of the UCS 200, for example, configuration source files 281 can be received at the configuration module 210 directly from the client, e.g., in UCS format with an identifier ($id) and a type ($type); whereas, in some embodiments, for example, the configuration source files 281 can be received at a configuration management service 220, discussed later below, that formats the client-generated configuration source files 281 and creates a (set of) formatted configuration source file(s) 210 that are provided to the configuration module 210.

In various example embodiments of the UCS 200, the metadata configuration module 212 is designed external to the configuration module 210 to provide (describe) the structure and rules of a configuration process. For example, the Config Metadata 212 provides metadata, also referred to as "Config Metadata" that is consumable by any services that needs to understand the configuration rules and structure of the enterprise software platform. For example, the repo (tool built on top of a repository) is written in typescript and published as an npm package. In implementations of the metadata configuration module 212, the metadata for a configuration domain is declared as a Model Definition, which describes the attribute schema, the relationships to other config domains, and uniqueness constraints that are enforced across a collection of domains. The Model Definition declared by the metadata configuration module 212 is used by the configuration module 210 to validate the set of source files and build the validated set of configuration source files (at process 215) into an artifact 251, also referred to as "Config.json", e.g., stored in a memory 250). The Workflow 1 can conclude at the process 219 where the validated configuration data set is persisted to the enterprise software platform 190 by the configuration deployment module 260, In an example structure of a Model Definition, a resource type can define each domain type (e.g., typically the name of the database table to be stored in). This can be the same $type attribute that is defined for the config object in the config source files. The structure of a Model Definition can include an attribute schema component that describes and validates the attributes of a configuration domain (e.g., except foreign keys), which can be structured to follow a specific schema format, e.g., JSON Schema format. The structure of a Model Definition can include a relationships component that describes the relationships this config entity has with other entities. In some examples, the relationship is presented as an object where the key is the name of the config domain and the value is the relationship type | relationship definition. The structure of a Model Definition can include a constraints component, in which each entity may have at least one unique constraint defined in a list for this component. In some examples, each constraint may have more than one key, which can be structured in an array of arrays. The first constraint in the list can be used to generate internal (pre-deployment) identifications. The structure of a Model Definition can include a transient attributes component, which are used for specifying attributes of a configuration that are to be deprecated (e.g., not in a final Model Definition), but might be needed to be processed when older configuration source files are migrated into newer configurations.

Figure 2B:
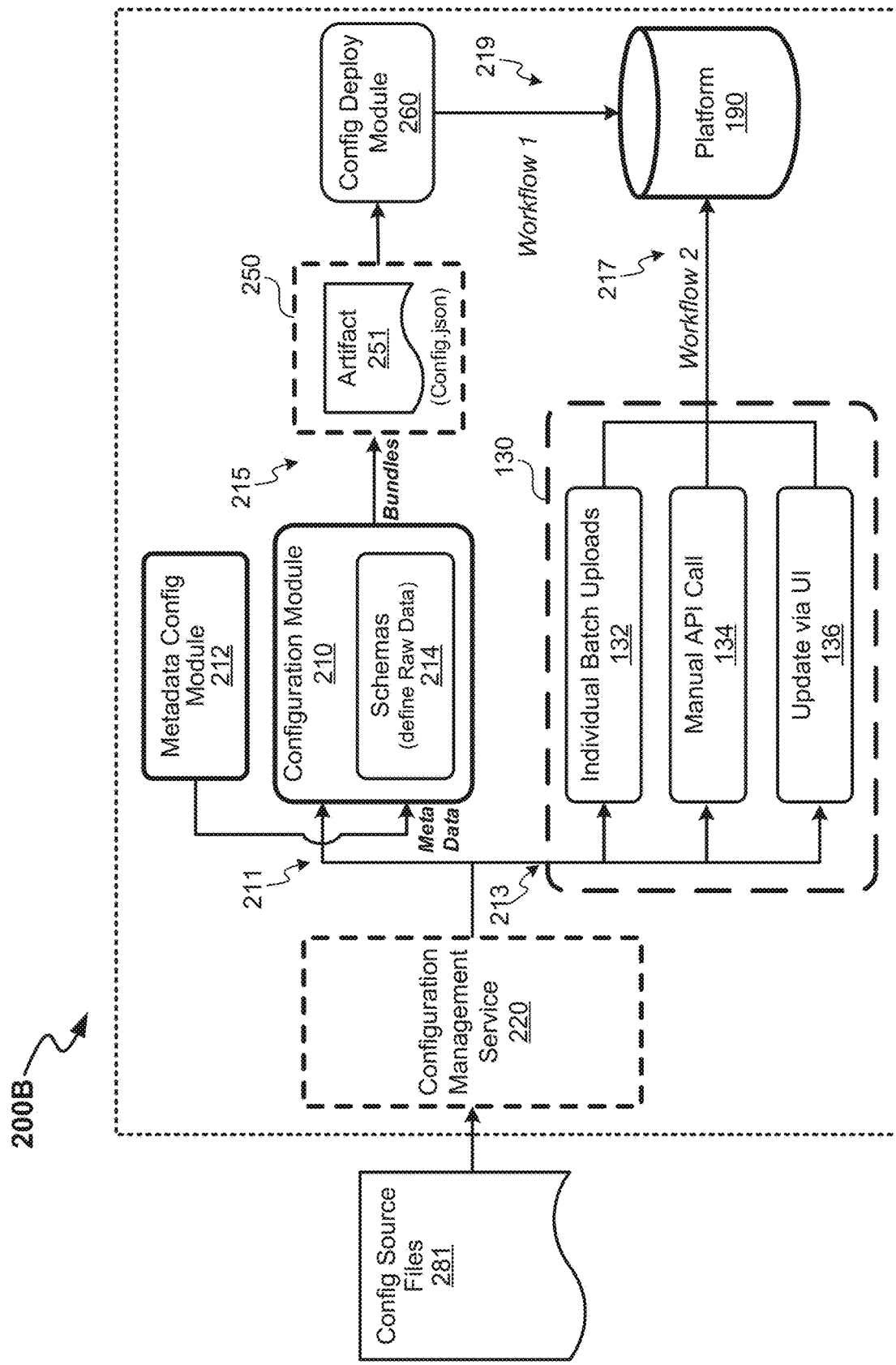
FIG. 2B shows a diagram depicting another example embodiment of a unified configuration system for managing a client configuration of enterprise software configured in accordance with some implementations of the present technology.

FIG. 2B shows a diagram depicting another example embodiment of the UCS 200, referenced in FIG. 2B as UCS 200B, that is configured in accordance with the present technology. The UCS 200B is configured to implement Workflow 1 and Workflow 2, e.g., whether in parallel, sequentially in any order, or a combination of parallel and sequentially. The UCS 200B includes the data configuration module 130 to manage (e.g., update) permissions, roles, users, and/or fixtures in accordance with the configuration of the client's version of the application that is managed by the configuration module 210. In such implementations of the Workflow 2 by the UCS 200B, for example, the services of the data configuration module 130 configure the client configuration data at the process 213 and persist the client configuration data to the enterprise software platform 190 at the process 217.

Figure 3A:
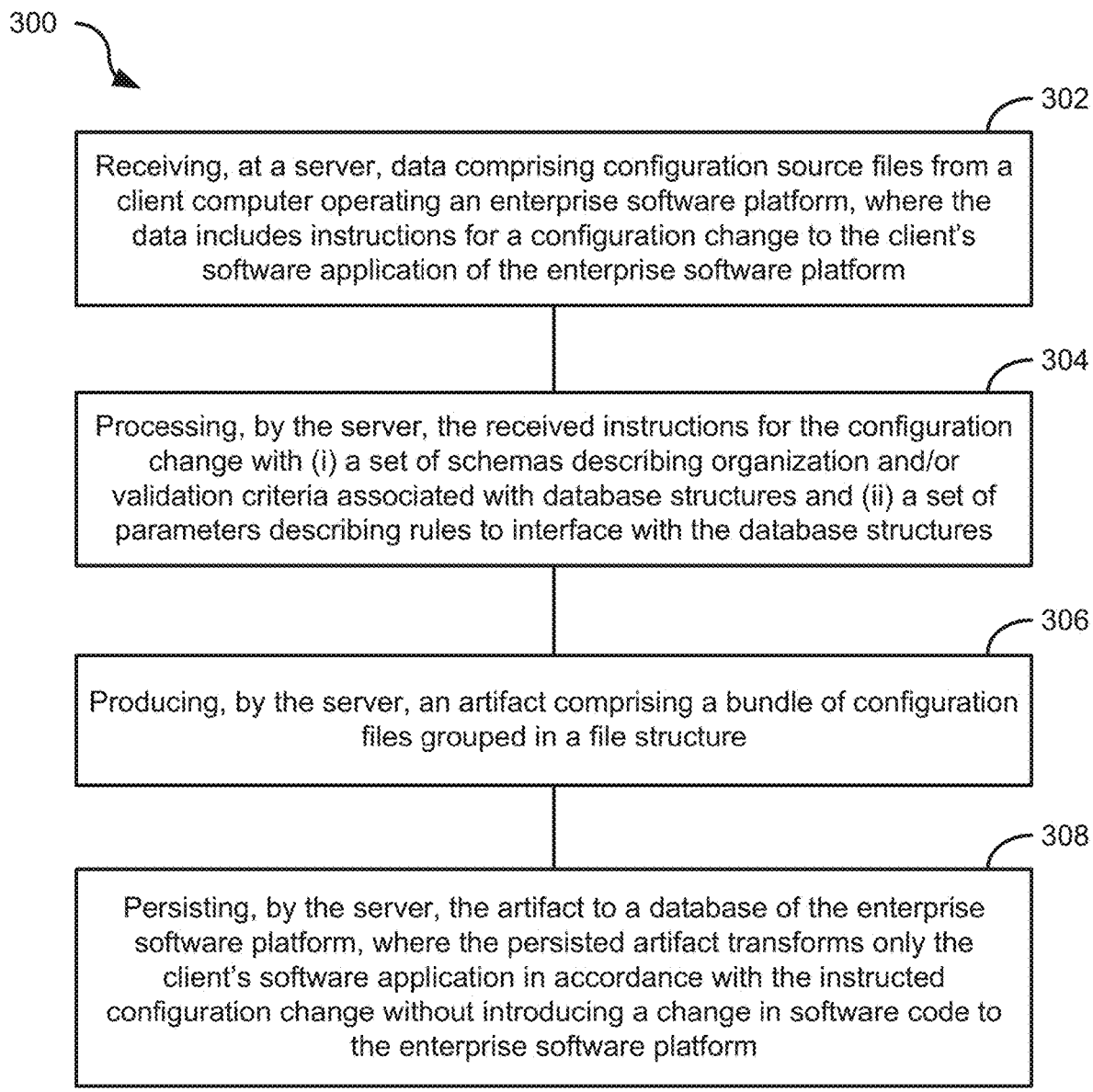
FIG. 3A shows a data flow diagram illustrating an example embodiment of a method for implementing a unified configuration of a client's enterprise software application of an enterprise software platform configured in accordance with some implementations of the present technology.

FIG. 3A shows a data flow diagram illustrating an example embodiment of a method 300 for implementing a unified configuration of a client's enterprise software application of an enterprise software platform configured in accordance with some implementations of the present technology. The method 300 includes a set of operations or processes 302-308. For some implementations of the method 308, for example, the operations or processes 302-308 may be implemented in a different orders or sequence or may overlap than the order or sequence shown in FIG. 3A.

The method 300 includes a process 302 to receive, at a server implementing an enterprise software platform (e.g., server of the UCS 100 or 200), data comprising configuration source files from a client computer (e.g., computer 180) operating a software application (tenant instance) the enterprise software platform, where the data includes instructions for a configuration change to the client's software application of the enterprise software platform. The method 300 includes a process 304 to process, by the server, the received instructions for the configuration change with (i) a set of schemas describing organization and/or validation criteria associated with database structures and (ii) a set of parameters describing rules to interface with the database structures. For example, in implementations of the process 304, the server (e.g., the configuration module 110 or 210) uses the metadata to validate the data represented in the source files. The method 300 includes a process 306 to produce, by the server, an artifact comprising a bundle of configuration files grouped in a file structure, e.g., a serialization of the data represented in the received source files. The method 300 includes a process 308 to persist, by the server, the artifact to a database of the enterprise software platform, wherein the persisted artifact transforms only the client's software application in accordance with the instructed configuration change without introducing a change in software code to the enterprise software platform. For example, in implementations of the process 308, the server (e.g., the configuration deployment module 160 or 260) breaks down the artifact based on each domain to perform additional validation checks (e.g., on one or both of the structure and the content of the data).

Figure 3B:
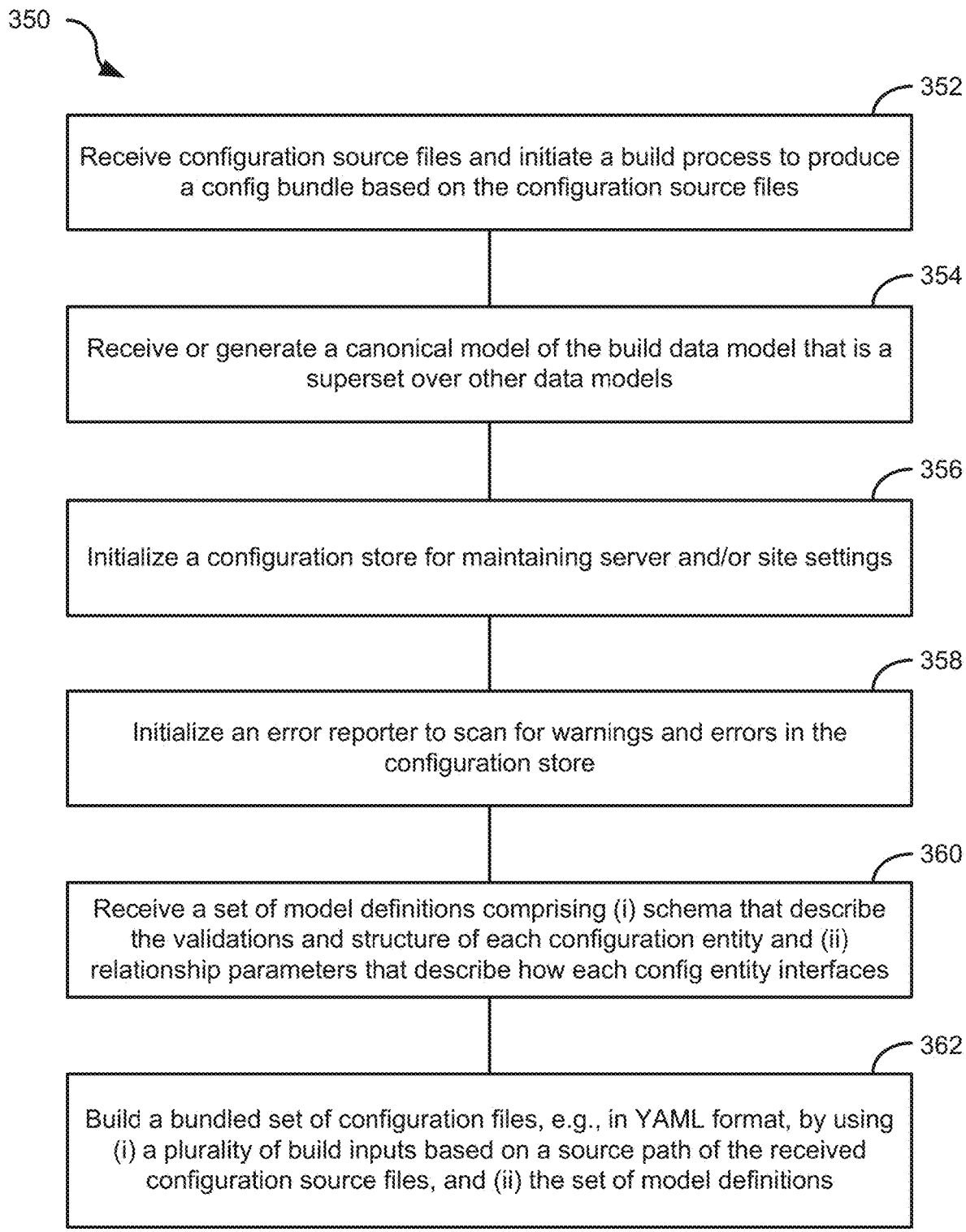
FIG. 3B shows a data flow diagram illustrating an example embodiment of a method for building a user-specified bundled configuration of an enterprise software application for an enterprise software platform configured in accordance with some implementations of the present technology.

FIG. 3B shows a data flow diagram illustrating an example embodiment of a method 350, implementable by the configuration module 210 of the UCS 200 or the configuration module 110 of the UCS 100, for building a user-specified bundled configuration of the software platform, in the form the artifact 251 (e.g., Config.json). The method 350 can be implemented for some implementations of the processes 304 and 306 discussed above in connection with FIG. 3A, The method 350 includes a set of operations or processes 352-362. In implementations of the method 350, for example, the operations or processes 352-362 can be implemented in various orders or sequences, but with the process 362 implemented last among the processes 352-360.

Referring to FIG. 3B, the method 350 includes a process 352 to receive user-specified configuration source files, e.g., at a configuration module of an example embodiment of the disclosed unified configuration system, and initiate a build process to produce a config bundle based on the configuration source files. The method 350 includes a process 354 to receive or generate a canonical model of the build data model that is a superset over other data models. The method 350 can include a process 356 to initialize a configuration store for maintaining server and/or site settings. The method 350 can include a process 358 to initialize an error reporter to scan and/or identify for warnings and errors in the configuration store.

In example implementations of the process 358, the types of errors the error reporter can identify include uniqueness constraint error, a broken relationship error, and a schema violation error. For example, a uniqueness constraint error can be shown when two config objects of the same resource type have the same identifier (e.g., $id) or have the same values for uniquely constrained attributes as defined in the metadata). For example, a broken relationship error can be shown when a config object does not specify a necessary relationship to another config object, and the referenced config object does not exist. For example, a schema violation error can be shown when the config object attributes are missing, or they do not adhere to the schema's attributes (e.g., in its Model Definition) in the metadata.

The method 350 includes one or more processes 360 to receive or generate a set of model definitions comprising (i) schema that describe the validations and structure of each configuration entity and (ii) relationship parameters that describe how each config entity interfaces. Implementations of the process 360 can include receiving configuration metadata 212. For example, the received or generated model definitions at the process 360 can include the example embodiments of the Model Definitions described above.

The method 350 includes a process 362 to build a bundled set of configuration files, e.g., in YAML format, by using (i) a plurality of build inputs based on a source path of the received configuration source files, and (ii) the set of model definitions, e.g., including the schema of attributes, constraints, and relationship parameters. YAML is a data serialization language that is commonly used for writing configuration files. While the embodiments described herein use YAML, format for configuration files, it will be appreciated that other suitable file formats and/or coding languages can be employed. An example embodiment of the process 362 is described below in FIG. 3C.

Figure 3C:
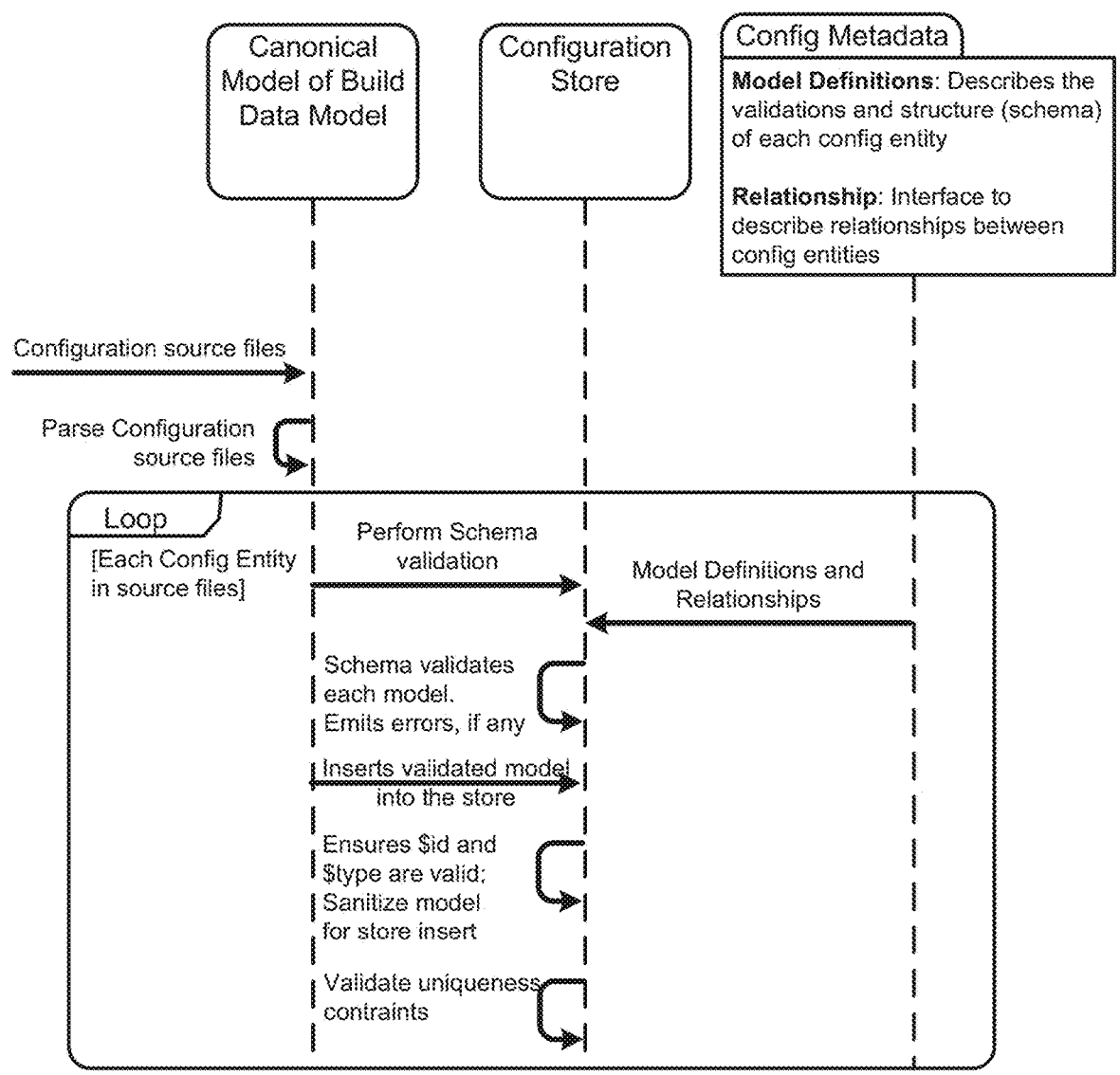
FIG. 3C shows a diagram depicting an example method for building a bundled set of configuration files configured in accordance with some implementations of the present technology.

FIG. 3C shows a diagram depicting an example method for implementing the process 362 for building a bundled set of configuration files. As illustrated in the diagram, the process 362 can include, after receiving the configuration source files (e.g., at the configuration module 210 or configuration module 110), parsing the configuration source files. The parsed data can then be processed to perform validation from the received model definitions, which include the schema describing the structure and rules for validating a configuration entity with the enterprise software platform. For example, the process 362 can include, after receiving the model definitions and the canonical model of build data, using the schema to validate each data model, where errors (if any) are emitted. The validated model(s) are then ready to be inserted. into the configuration store. For example, the process 362 can include sanitizing the model(s) to ensure the identity and type are valid. The process 362 can include validating the uniqueness constraints.

Referring back to FIG. 2A, in some example embodiments of the UCS 200, the UCS 200 includes a configuration management service (CMS) 220 that is designed to unify the different config source file update pathways into a single transaction, which is automated such that a user (e.g., deployment engineer or other sophisticated administrator on the client side) does not have to manage unification of new configurations with the enterprise software platform. For example, the CMS 220 can receive config source files in any structure that complies with a canonical format (i.e., rules) of the UCS 200.

In some implementations, the CMS 220 can be configured to provide a service that allows an intermediary client computing device to act on behalf of multiple end-user client computing devices associated with different end user entities, such that the intermediary client computing device's user (e.g., having verifiable access privileges) is able to deploy target configuration deployments towards various different environments, different tenants, belonging to one or more customers, at will, and thereby not requiring the client-side user to be versed on the specific protocols of the enterprise software platform.

The CMS 220 is able to process UCS-format configuration source files 281, which include a standard identification (ID), e.g., shown as $id $type. The standard ID of the UCS-format configuration source files 218 allows for the compilation of and reading into those configuration source files such that they are not dependent on the structure itself.

In some embodiments, for example, the CMS 220 can include a configuration migration tool (CMT) that uses a prior bundled configuration data (e.g., artifact 251 or artifact 151) that is created by the configuration module (e.g., configuration module 210 or configuration module 110) for modifying (e.g., formatting) new configuration source files that use a canonical format. These modified configuration source files can then generate the same bundled configuration data using the configuration module, which will be used to migrate the pre-existing customer configurations. An example implementation of the CMT for formatting client-provided configuration source file is shown in FIG. 4.

Figure 4:
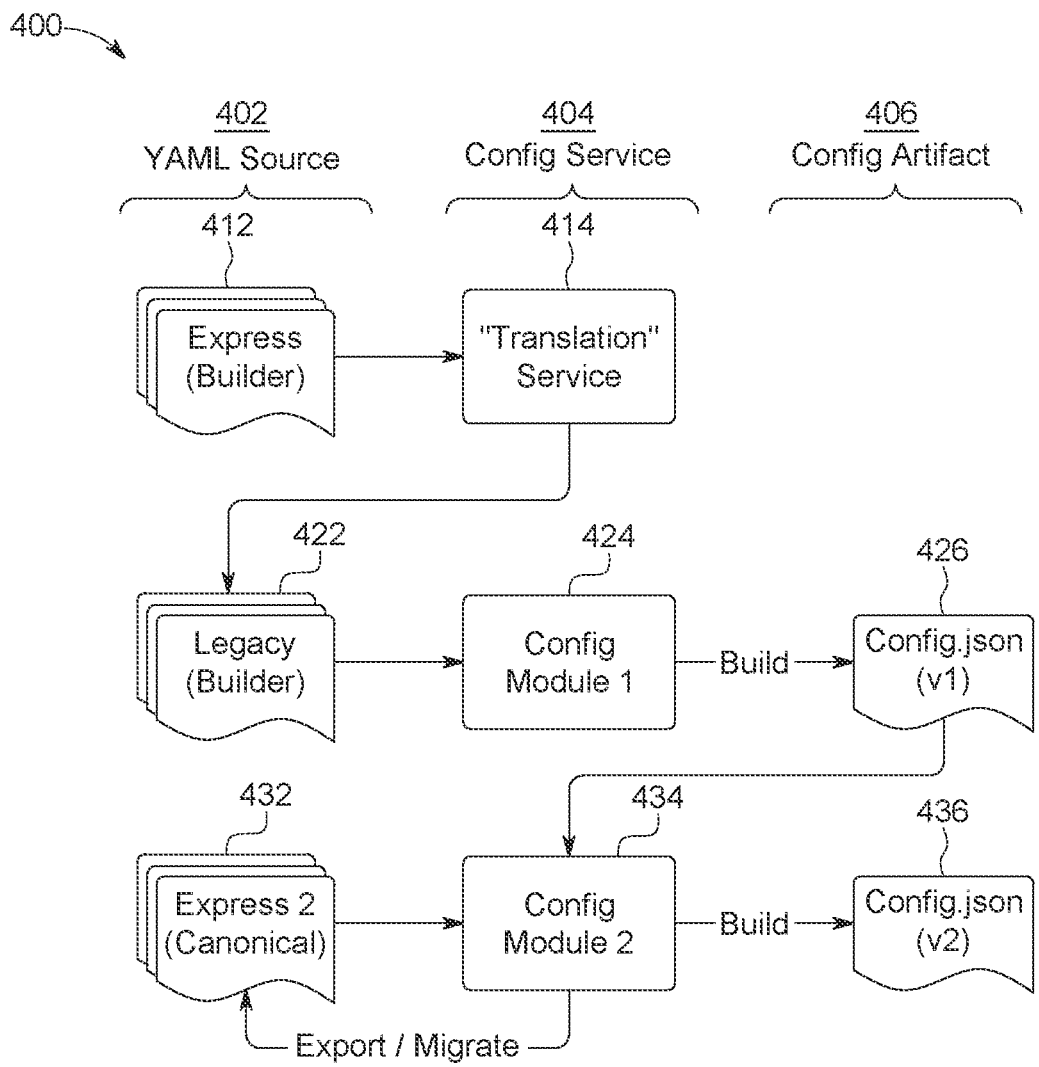
FIG. 4 shows a diagram illustrating an example implementation for formatting configuration source files by a configuration migration method in accordance with some implementations of the present technology.

FIG. 4 shows a diagram illustrating an example processing design 400 for formatting configuration source files by a configuration migration method in accordance with the present technology. The processing design 400 includes data flow and processing for configuration source files 402 (e.g., which can be YAML files), a configuration service 404, and a bundled configuration artifact 406. In one process design, configuration source files 414 are in an express structure that a configuration management service (e.g., CMS 120 or 220) translates to a legacy structure 422 that is received by a configuration module for a configuration service 424 (e.g., configuration module 110 or 210) to be built into an artifact 426 that is a bundled set of configuration files (that contains a large array of data model (e.g., database record uploadable in a single operation)). In some embodiments, the processing design 400 may include a second layer of configuration, where a configuration service 434 (e.g., by configuration module 110 or 210) builds a second artifact 436 based on the artifact 426 (i.e., an earlier build of the bundled set of configuration files) and additional configuration source files 432.

Referring back to FIG. 2A, in implementations of the UCS 200, for example, the configuration deployment module 260 persists the validated configuration source data to a non-volatile storage medium of the enterprise software platform 190. As used herein, persistence of data is the continuance or survival of data after the process with which it was created has ended. The configuration deployment module 260 includes one or more algorithms that persists the bundled configuration artifact 251 (e.g., Config.json) over multiple phases. For example, the configuration deployment module 260 first ingests the new configuration bundle and converts all config objects in the bundle into a plurality of config model objects e.g., Config::Model objects) and a wrapper class for config objects, with helper functions. Next, the configuration deployment module 260 performs transformations on the list of config models. Finally, the configuration deployment module 260 persists all config models in the transformed config bundle correctly into the database of the enterprise software platform 190, e.g., stores the config models in the transformed config bundle in memory.

To persist different configuration objects in Config.json, the configuration deployment module 260 needs to be made aware about the type of the object and how to persist it. In sonic implementations, for example, this can be done by the configuration deployment module 260 adding an entry in a type-settings object in the type file, i.e., a type entry. For example, in some embodiments, the key of the type-setting object is the resource type of the object, which is the same as the model definition of the configuration domain, e.g., in the metadata configuration module 212. The value of type-setting object entry has multiple parameters, which can include (but is not limited to) the following, for example: (i) an active record class parameter that is the name (e.g., string) of the model into which the configuration deployment module 260 persists the type; (ii) a unique key parameter (e.g., array including symbols) that provides a list of attributes (e.g., symbols) uniquely identifying the configuration object; (iii) an index name parameter (e.g., string) that is used to resolve conflicts for update; (iv) an automatic identification parameter that is a Boolean which toggles whether an ID is generated for models created during a transformation; and (v) a persist strategy parameter e.g., symbol), which is the manner which to persist, e.g., including by insert, read only, and merge. In some embodiments, the multiple parameters of the type-setting object can optionally include a support import parameter (e.g., Boolean) that checks if the type is able to be persisted (e.g., is true or false) in determining whether to insert or merge the data to be persisted. In some embodiments, for example, the multiple parameters of the type-setting object can optionally include a fixture parameter (e.g., Boolean) that checks if the type entry is a fixture, which is not necessarily persisted.

In some implementations, for example, the bundled configuration artifact 251 (e.g., Config.json) being uploaded may not immediately be able to be persisted. In such cases, new config data may be incoming and in the processing pipeline that could affect persisted data. As such, the UCS 200 is designed to adapt in such cases by transformation of the config models and thereby change the data or create new models (e.g., join tables, internal models, etc.) based on the incoming data. These transformations to the config bundle can be implemented before persistence of the data.

For example, in some embodiments, the configuration deployment module 260 is designed to map the bundled configuration artifact 251 (e.g., Config.json) to data that is persistable in the database of the enterprise software platform 190. The transformation method can include adding and/or removing config models based on the newly-received (incoming) data, and adding attributes and relationships to the config models. In such implementations, for example, the transformed config models can inherit from the same parent class, and/or may be renamed under a naming convention that includes "transform" or derivation or signifying thereof in the filename. The transformation method allows for different techniques for querying, adding, and removing config objects from the bundle before it is persisted into the database. For example, implementation of a type query (command) can return an array of all models with the specified config type in the bundle; implementation of an add config model (command) can add a config model to the bundle having certain specified attributes (and, optionally, relationships), as specified in the command; and implementation of a remove config model (command) can remove a config model(s) with the specified attributes from the bundle, as specified in the command. In some implementations, for example, it may be necessary to add a relationship to a config model, which can be done through the transformation method, e.g., by an add relationship command.

In some embodiments of the UCS 200, for example, the UCS 200 can optionally include a testing module (not shown in FIG. 2A) that tests whether a bundle to be persisted in the database of the platform 190 contains all the data objects expected by the domain's data schema, after the transformations have run. Since the transform is the final layer where the UCS 200 edits the configuration bundle before it is persisted, the configuration deployment module 260 can be configured to produce a copy of the transformation output data to be persisted, such that the testing module receives the copy and runs the test protocol on the copy. In some examples, each test should contain a shared context with the transform that sets the subject to a function that runs the transform on the config variable and returns the resulting. For example, the config variable is an array of config objects, as it would be expected in the bundle. In some embodiments, for example, the testing module can also set an options variable, which is for any extra parameters that might be needed in the transform.

In example implementations of the UCS 200, the transformation method can create and link config objects representing any join tables or dependent internal models that are not configured in the source files. The transformation method can be used when creating a new config domain in which the models do not carefully reflect real world objects, e.g., where the data from the config source files are easily persisted directly from the bundle. When transformations occur, for example, the transformation method can account for inter-dependency of a present transformations on the result of one or more prior transformations.

The disclosed embodiments of the UCS (e.g., including the UCS 100 and the UCS 200) provide unified workflow and scheduling configuration tooling that are expected to significantly reduce the amount of data processing required to configure the multitude of different client-specific configurations for an enterprise software platform. Due to interdependencies in configuration data models, a streamlined, facile, and automated method to update and/or reconfigure software application configuration is needed to reduce complexity while ensuring accuracy. For example, in implementations of a personal therapy management software application, business process model and notation (BPMN) files are typically used to define what the steps are implemented (e.g., workflows) for a client's configuration of their software application of the enterprise software platform. The configuration workflows can include YAML files that reference these BPMN steps and add more configuration to them. Yet, this is hard dependency where, if a BPMN file is changed, e.g., to remove a step or to rename a feature, this could break the workflow operability of the configuration without accounting for this change in the entire workflow(s).

Such challenges are addressed by the disclosed embodiments of the UCS. For example, the UCS 100 is operable to process, validate, and persist bundled changes to client-desired configuration of the software application, where the configuration module 110 generates a final configuration structure and an interim builder structure, e.g., which is the structured set of editable YAML files, and converts and runs transformations to ultimately produce a JSON artifact (which contains a large array of data model (e.g., database record uploadable in a single operation)); and where the configuration deployment module 160 persist the database records directly to the platform database 190, e.g., since the UCS 100 is cleanly maps the data models to the database tables.

Similarly, for example, the UCS 200 is also operable to process, validate, and persist bundled changes to the client-desired configuration of the software application. The configuration module 210 is capable of generating a final configuration structure and building the configuration in a more efficient manner. The UCS 200 includes an architecture where knowledge of the data structures, rules and/or transformation logic (e.g., the structure of the YAML files for configuring the enterprise software platform), which affect the mapping of the configuration data in the database of the platform 190, are stored outside of the configuration module 210 (i.e., by the metadata configuration module 212), such that changes to this knowledge can be made independent of the configuration module 210. For example, this allows the configuration module 210 to be protected against constant or continuously changing schemas, e.g., such as changing feature assignments and/or new capabilities to the client's software application configuration.

Figure 5:
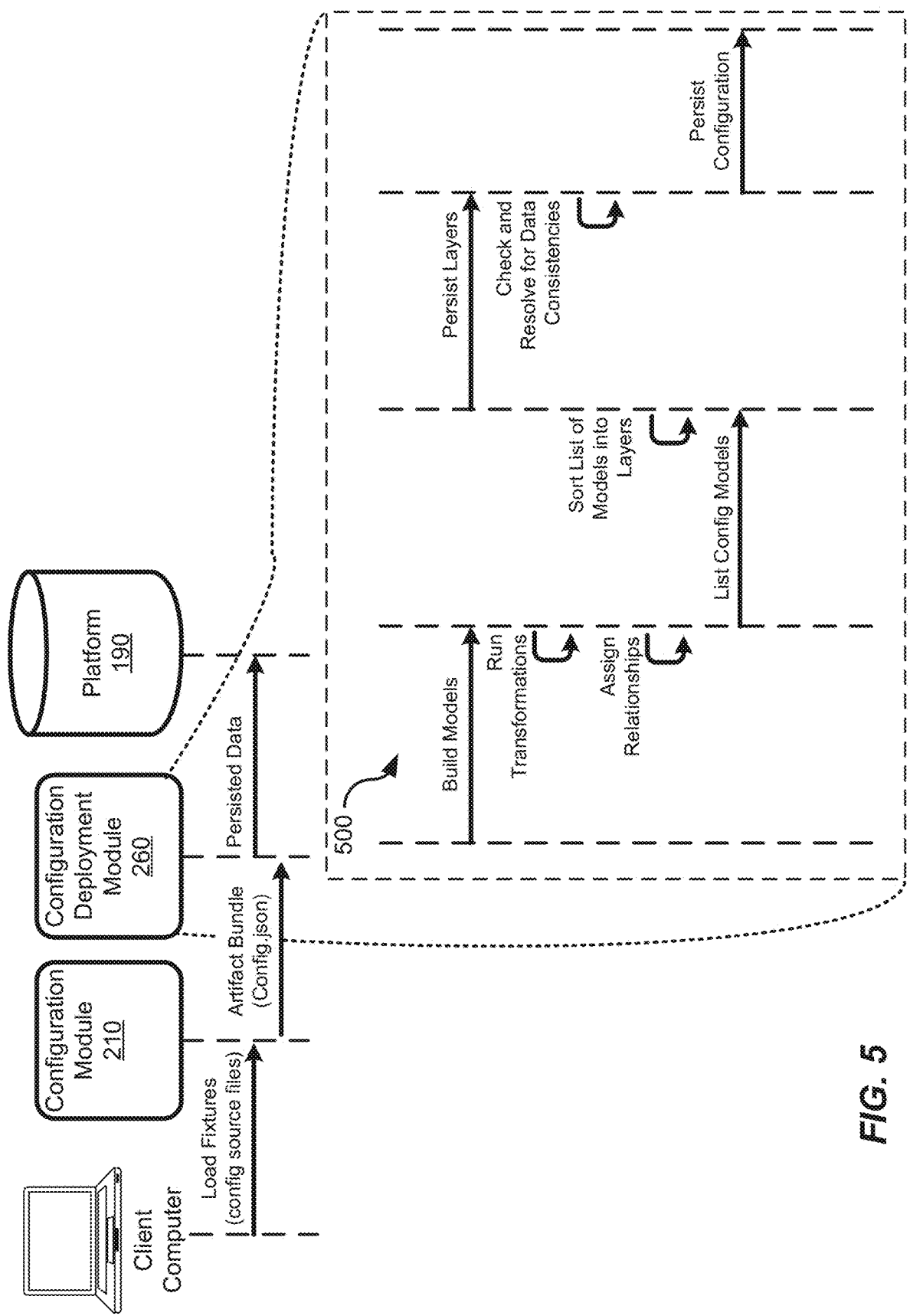
FIG. 5 shows a data flow diagram illustrating an example implementation of persisting data by an example unified configuration system to a non-volatile storage medium of an enterprise software platform.

FIG. 5 shows a data flow diagram illustrating an example implementation 500 of the configuration deployment module 260 for persisting the validated configuration source data to a non-volatile storage medium of the enterprise software platform 190.

From the Config.json bundled set of configuration files, the configuration deployment module 260 builds configuration models with model structures that the enterprise software platform 190 is familiar with. The configuration deployment module 260 then runs transformations on the configuration models built from the Config.json to be modified to a data structure that is compatible with those known to the enterprise software platform 190. As part of the transformations of the configuration models, the configuration deployment module 260 assigns relationships to the modified data structure based on a role of the data with the system. Implementations of these processing steps are run in memory, e.g., memory 150 or memory 250 of the UCS 100 or 200, respectively. Next the configuration deployment module 260 creates a list of the configuration models that is analyzed for sorting into layers. For example, in some implementations, the list of configuration models are sorted topologically, where the data entities (of the configuration models) that have the least amount of associations or dependencies to other data entities in the list are given a higher place on the list (e.g., where the first object on the list could be an object with no associations, and where the last object in the list may have the most associations to other data and/or be a root of the data). In this manner, for example, the sorting effectively ensures the data consistency. Yet, nevertheless, in the example implementation 500, the configuration deployment module 260 persists (e.g., saves in a separate portion of the memory 150, 250) the sorted layers and after which checks for data consistency (and resolves any inconsistencies, if any). For example, in sonic implementations, the configuration deployment module 260 can run analytics from layer to layer and back link any associated data entity shown not to be consistent from the prior check. Finally, the configuration deployment module 260 runs a persist strategy to persist the checked data in the enterprise software platform 190 (e.g., save the built/sorted/validated configuration models from the memory 150, 250 in the database of the enterprise software platform).

Figure 6A:
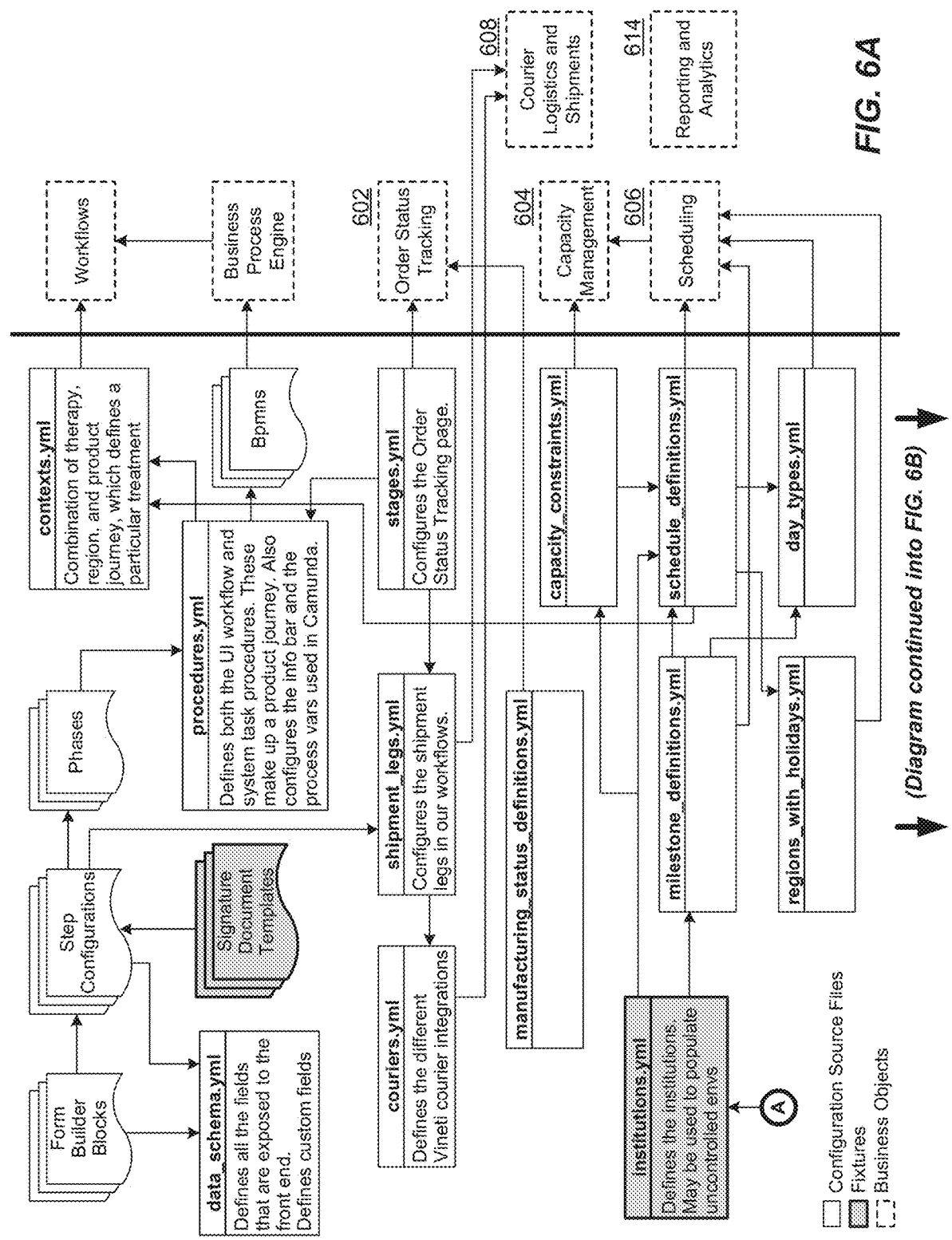
FIGS. 6A and 6B, together, illustrate a data flow architecture of an example configuration implementable by the disclosed unified configuration system for a personal therapy management enterprise software application and platform configured in accordance with the present technology.
Figure 6B:
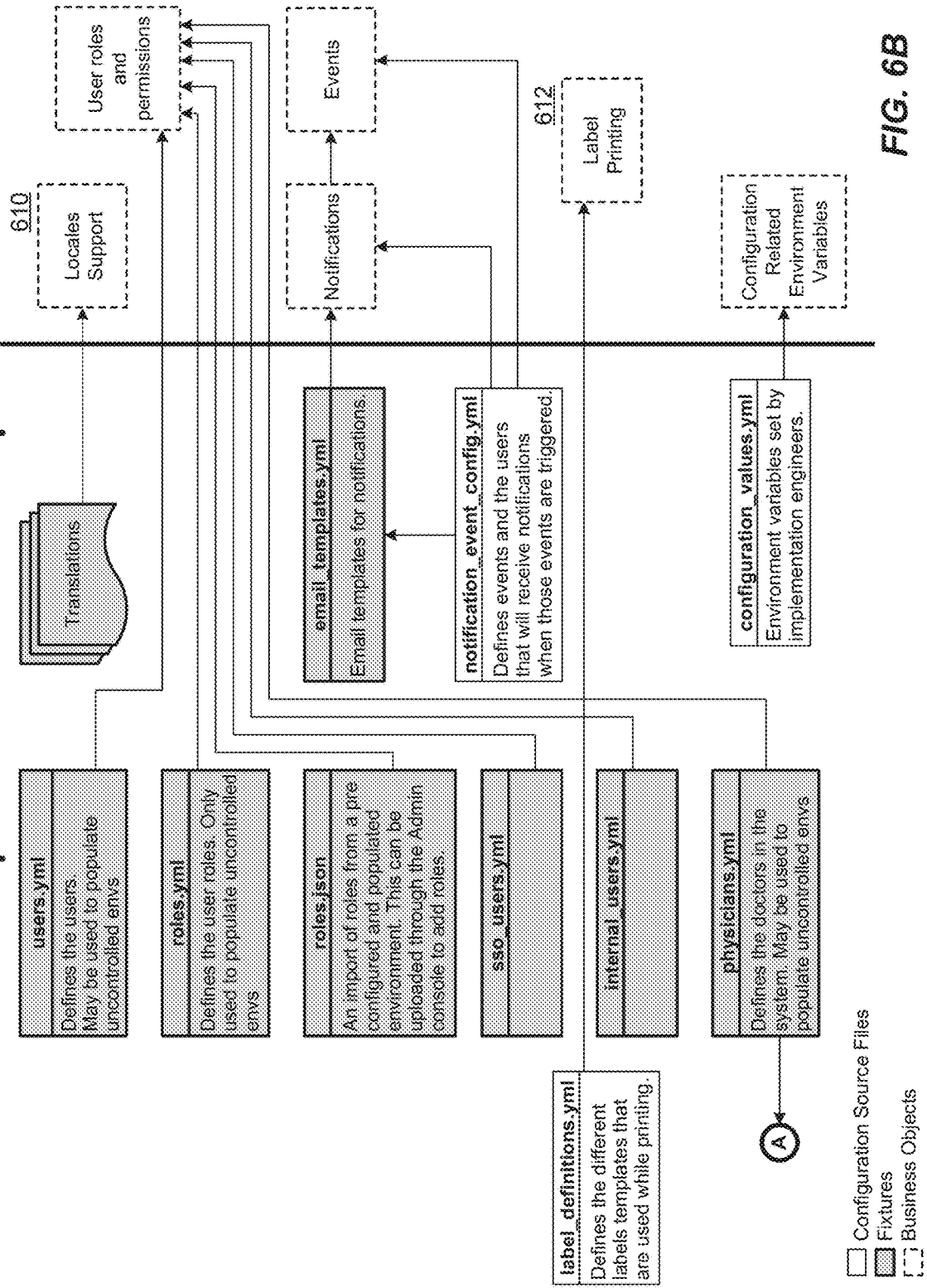

FIGS. 6A and 6B show a diagram (spread across both FIG. 6A and FIG. 6B) that illustrates a data flow architecture of an example configuration implementable by the UCS 100 and the UCS 200 for a personal therapy management enterprise software application and platform. In this example, BPMN objects representing steps in personalized therapy management (illustrated in broken-line boxes, shown on the right side of the diagram) can include certain processes in an orchestrated supply chain management system for fulfilling a vein-to-vein personalized medicine treatment, including Order Tracking Status 602, Capacity. Management 604, Scheduling 606, Courier Logistics and Shipments 608, Locales Support 610, Label Printing 612, Reporting and Analytics 614, and other tools. The BPMN objects are linked to configuration workflows (illustrated by lines with arrows between various fixtures (in shaded-solid boxes and configuration source files (in unshaded-solid boxes), e.g., in which the fixtures and/or configuration source files may be represented by YAML files in this example. The configuration workflows reference the steps associated with the BPMN objects to create the client-desired configurations determined by configuration source files and fixtures. The configuration source files allow the client to configure their software application by, for example, setting up and/or modifying the institutions that are involved in the personalized medicine supply chain, setting up and/or modifying the rules and permissions for users (of various stakeholders) in the supply chain, and setting up and/or modifying the manner to which each stakeholder can interact (interconnectivity). Some examples of the stakeholders and the supply chain for personalized therapy management are discussed below.

Chain of Identity and Chain of Custody Management

In personalized therapeutics, safety and efficacy rely on the right patient receiving the right treatment. The process of tracking and matching materials in the supply chain is driven by a concept known as Chain of Identity (COI), which is the permanent, transparent association of a patient and/or donor's unique identifiers to their tissue and/or cells from order through collection, manufacturing, administration, and post-treatment monitoring. Pairing COI with Chain of Custody (COC), which is the permanent data capture of tracking and handling information for a therapy at every step, can provide a truly traceable, trustworthy process.

Figure 7:
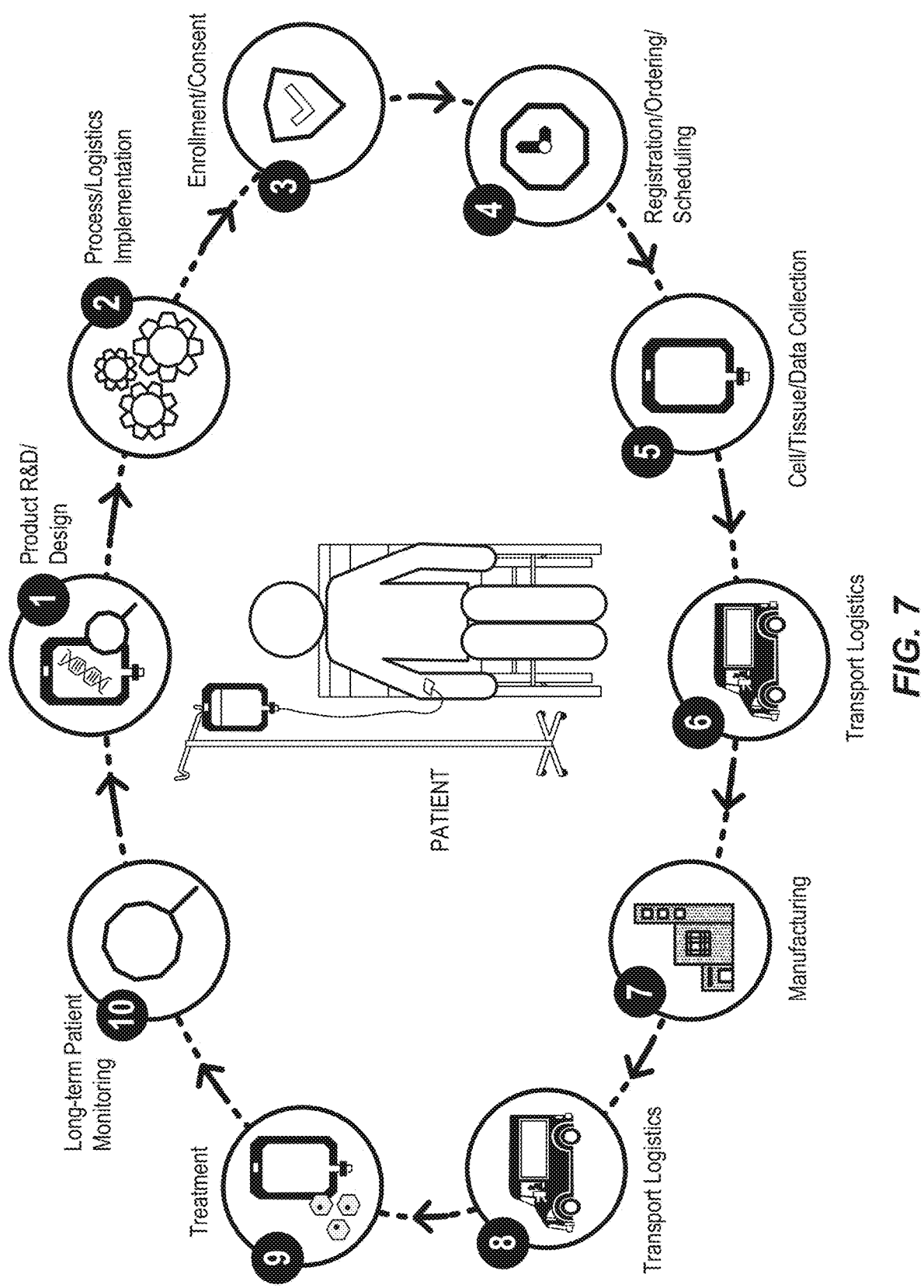
FIG. 7 shows a diagram illustrating an example process for implementing a personalized therapy.

FIG. 7 shows a diagram illustrating an example process for implementing a personalized therapy, e.g., depicting various stakeholders and/or transactions in a supply chain across a "vein to vein" to therapy cycle. For example, when a personalize therapeutic product and procedure is devised for a patient (event 1), various concurrent and sequential actions must begin to implement the personalized therapy process (event 2) to coordinate the logistics of the personalized therapy. For example, the patient is enrolled and consents to the prescribed personalized therapy by the HCP (event 3), after which registration, ordering, and scheduling commences (event 4). The scheduling, for example, can set dates for key events, such as the extraction of biological material from the patient (event 5), the transportation logistics (event 6) for providing the biological material to the personalized therapy product manufacturer for creation of the product (event 7), the transportation logistics (event 8) providing for the personalized therapy product to the treatment facility (event 9), and the long-term patient monitoring (event 10) to ensure the effectiveness in the personalized therapy treatment the patient's disease or condition.

Figure 8:
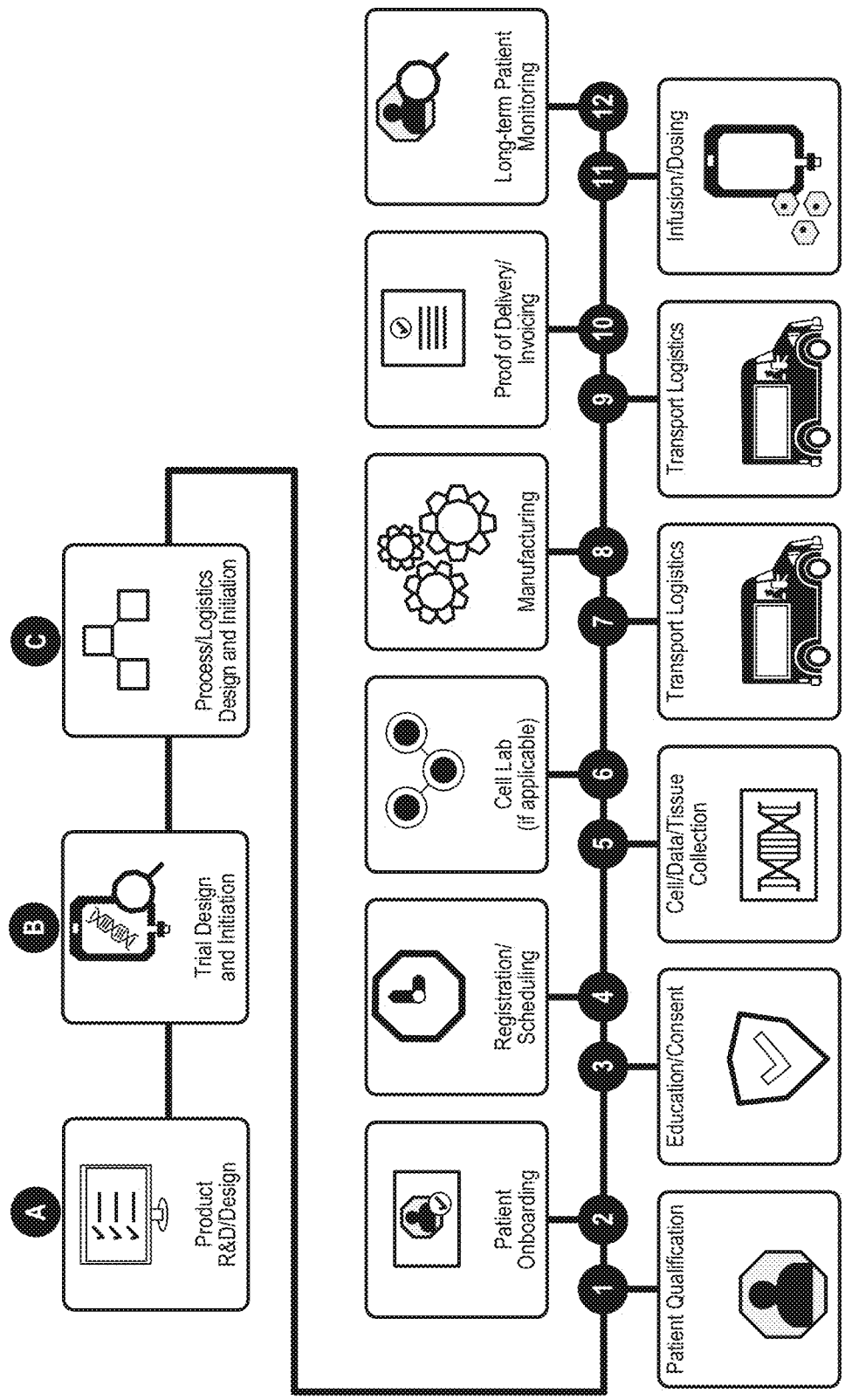
FIG. 8 shows a diagram illustrating another example process for implementing a personalized therapy.

FIG. 8 shows a diagram illustrating another example process for implementing a personalized therapy. The diagram of FIG. 8 illustrates events prior to implementation of a personalized therapy, including product research, design and development (item A), product trial design and initiation (item B), and process and logistics design and initiation (item C). The diagram of FIG. 8 also illustrates a modified sequence of events in the personalized medicine treatment process from that of FIG. 7.

At a basic level, Chain of Identity is enabled by a COI Identifier (COI ID), a set of numbers and/or characters that is the overarching "ID badge" for each patient and key materials related to their product. The COI ID must link a therapy to the intended patient and protect patient privacy. The COI ID is used in multiple places on the patient journey, from medical records to in-process drug labels.

The conventional approach to the structure and format for a COI ID is based on existing patient-specific, donation-based processes; an example is a bone marrow collection where the donated sample is used in the therapy. While existing approaches to COI ID are well-understood and utilized, they are not sufficient for present and future cell and gene therapies (CGTs). CGTs are more complex than other donation-based treatments. Some treatments may be patient-based, some may be donor-based, and some may be based on a mix of source materials. Some may be single-dose products, while others may be multi-dose products. Therefore, a new standard is needed for Chain of Identity management.

In some embodiments, a single COI ID that best meets the data needs of the patient, the site and the product that comprises three sub identifiers: a core ID, a treatment ID, and a specimen ID. The core ID (also referred to as core COI ID) includes a continuous string of multiple alphanumeric characters that uniquely identifies the patient receiving the therapy and the company and/or sponsor for the therapy product. The treatment ID includes a continuous string of multiple alphanumeric characters that uniquely identifies a specific treatment order cycle for a therapy, which is distinct part of the treatment journey. The specimen ID includes a continuous string of multiple alphanumeric characters that uniquely identifies each specimen involved in treatment, including cellular material, and any manipulation of that material, through to the final product.

Table 1 (shown below) illustrates an example embodiment of the single COI ID comprising the core ID, the treatment ID, and the specimen ID. In this example embodiment, the core ID includes a nine-character code beginning with a three-letter company identifier that is unique to a company/sponsor, followed by a six-digit core patient ID, which is unique to a patient for all of their product journeys. In this example, the treatment ID includes a five-character code, which trails the core ID (that may optionally include a dash "-" character), beginning with a three-letter product identifier that is unique to a product or therapy, followed by a two-digit order identifier, which indicates a specific treatment order cycle. Finally, in this example, the specimen ID includes a six-character code, which trails the specimen ID (that may optionally include a dash "-" character), beginning with a two-letter procedure identifier that indicates a procedure type and/or grouping of specimens, followed by a two-digit run identifier that indicates a specific session/run of a procedure type, and followed by a two-digit item identifier that indicates and item number produced in a session/run.

TABLE 1

CMP123456-PRD01-FP0201
- Core COI ID: CMP123456
- Treatment ID: CMP123456-PRD01
- Specimen ID: CMP123456-PRD01-FP0201

Core COI ID / Specimen ID / Specimen ID:

| Company identifier | Core Patient ID | Product identifier | Order identifier | Procedure identifier | Run identifier | Item identifier |
|---|---|---|---|---|---|---|
| Unique to a company / sponsor | Unique to a patient for all their product journeys | Unique to a product (or therapy) | Indicates a specific treatment order cycle | Indicates a procedure type and/or groupings of specimens | Indicates a specific session/run of a procedure type | Indicates item number produced in a session/run |

Example User Interfaces of UCS for Personalized Therapy Management Software

In some embodiments of the UCS, the system provides a graphical user interface (GUI) to accommodate a variety of different users of varying programming levels, e.g., including for technical and non-technical users on the client side to make configuration changes to their software application. For example, when a supply chain manager realizes a need for a change in the manufacturing production line, particularly if the matter was urgent, the GUI of the disclosed UCS can enable that supply chain manager to quickly implement the production line change such that it immediately is implemented in the platform, regardless of the supply chain manager's level of expertise in software coding.

FIGS. 9A-9F show diagrams illustrating graphical user interfaces for example embodiments of the disclosed unified configuration system, e.g., the UCS 100 and the UCS 200, designed for configuration of a personalized therapy management enterprise software application. Like features shown in some GUI images for certain figures may also be shown in other images in other figures.

Figure 9A:
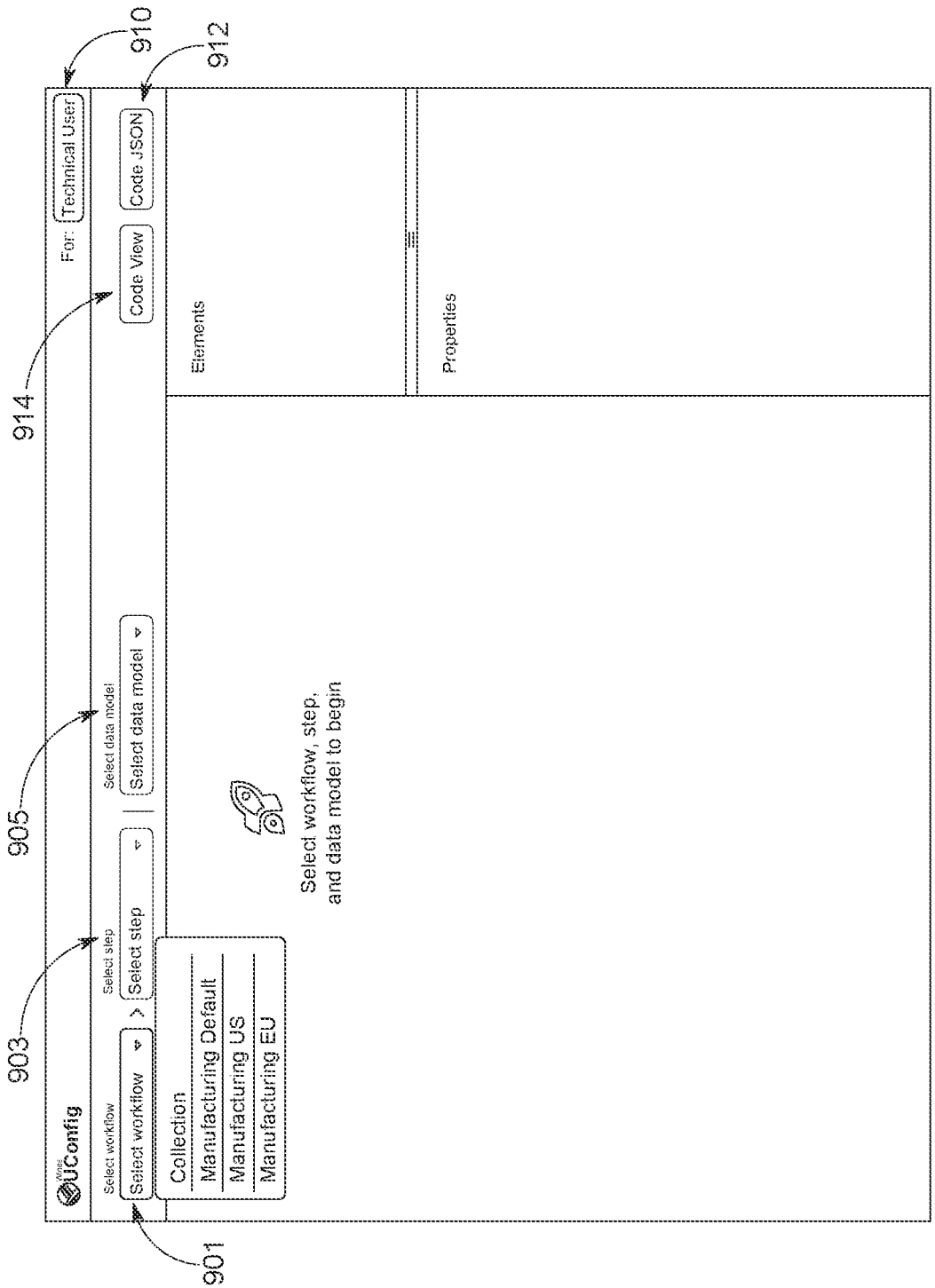
FIGS. 9A-9F show diagrams illustrating graphical user interfaces for an example unified configuration system designed for configuration of a personal therapy management enterprise software application configured in accordance with some implementations of the present technology.

Referring first to FIG. 9A, this illustration shows an example GUI for an example UCS, which includes a drop-down menu 901 to select a workflow (and/or add a new workflow) in configuring the software application, e.g., the personalized therapy management software application in this example. In the example of FIG. 9A, the menu 901 includes a list of workflows previously created, including (sample) collection and (product) manufacturing workflows, including a default manufacturing workflow and a US and EU manufacturing workflow. The GUI includes an input 910 that allows the user to select a skill level that can affect the GUI, such that the GUI may present a technical user more capabilities to enter and/or edit code (e.g., via a software code view in the GUI, discussed later), and the GUI may present a non-technical user with more graphical and pre-generated features to select from in making changes to the configuration.

Figure 9B:
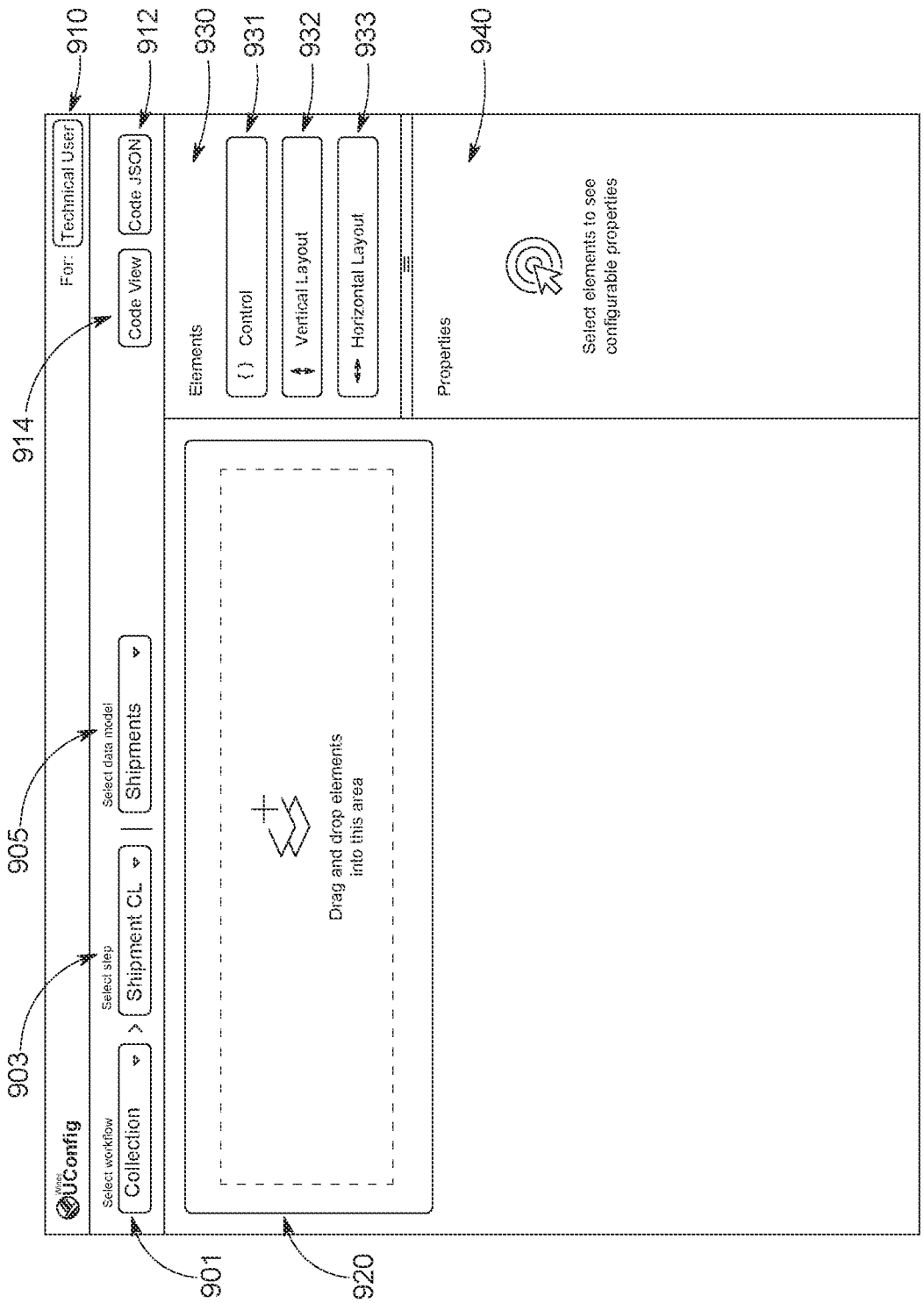

FIG. 9B shows an example GUI for the example UCS, which further illustrates related drop-down step menu 903 and drop-down data model menu 905, in which each menu relates to a selection in the prior menu. For example, selection of the "Collection" workflow in menu 901 creates a list in the menu 903 for selecting a particular step associated with the selected workflow in menu 901; and likewise, selection of a particular step in menu 903 creates a list in the menu 905 for selecting a particular data model. In this example, the drop-down menu 903 shows that the step "Shipment Checklist" was selected, and that the "Shipments" data model was selected in the menu 905.

Figure 9C:
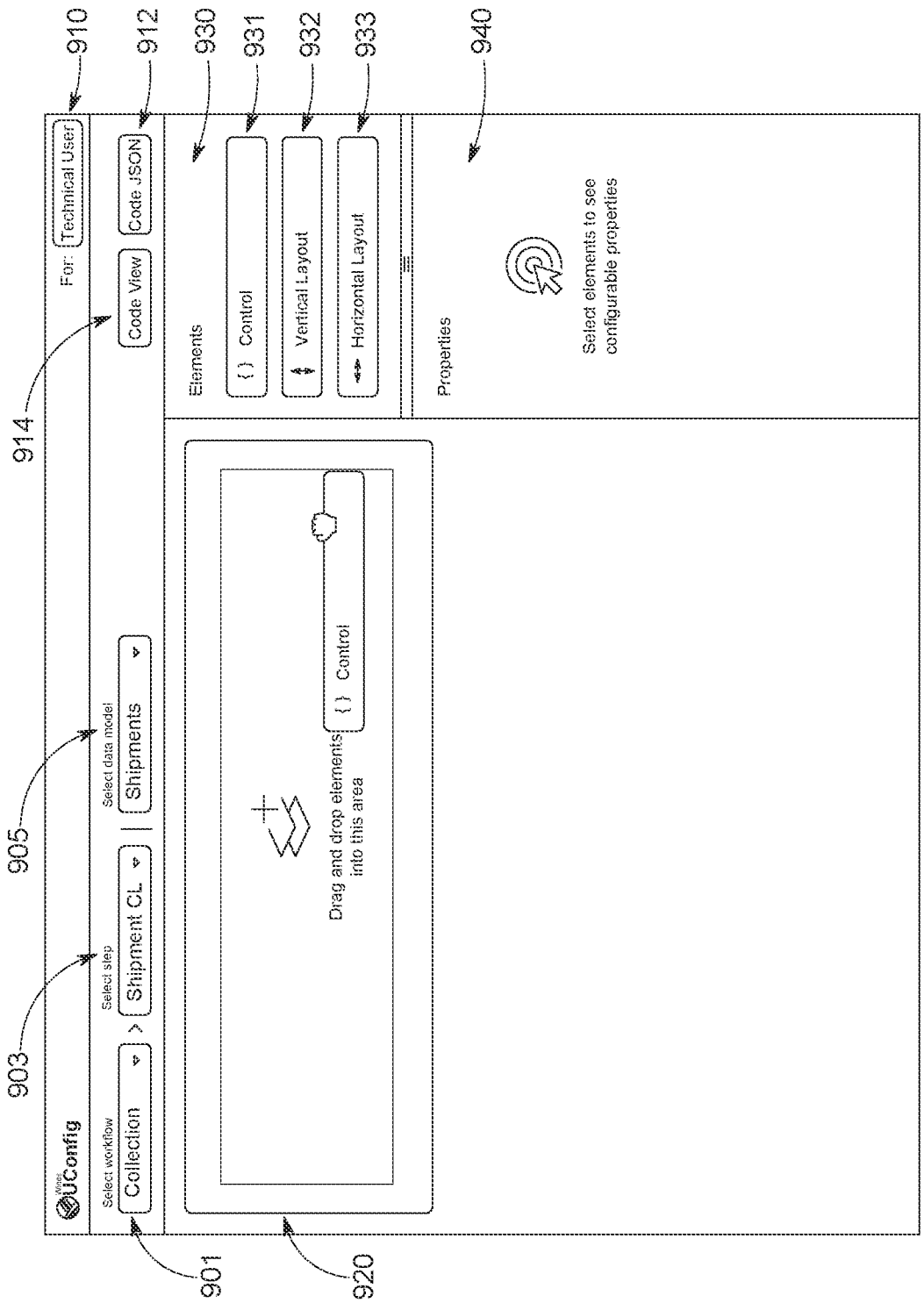

FIG. 9C shows an example GUI for the example UCS, which further illustrates graphical-based edits to the configuration in a configuration area 920 of the GUI. The configuration area 920 allows for elements (listed in Elements area 930, e.g., including a Control element 931, a Vertical Layout element 932, and a Horizontal Layout element 933) to be dragged and dropped, e.g., allowing a user to modify a workflow. In this example, a Control element 931 is being placed in the area 920. Also illustrated in this example GUI is a Properties area 940, which shows the configurable properties of an element in the Elements area 930 when selected.

Figure 9D:
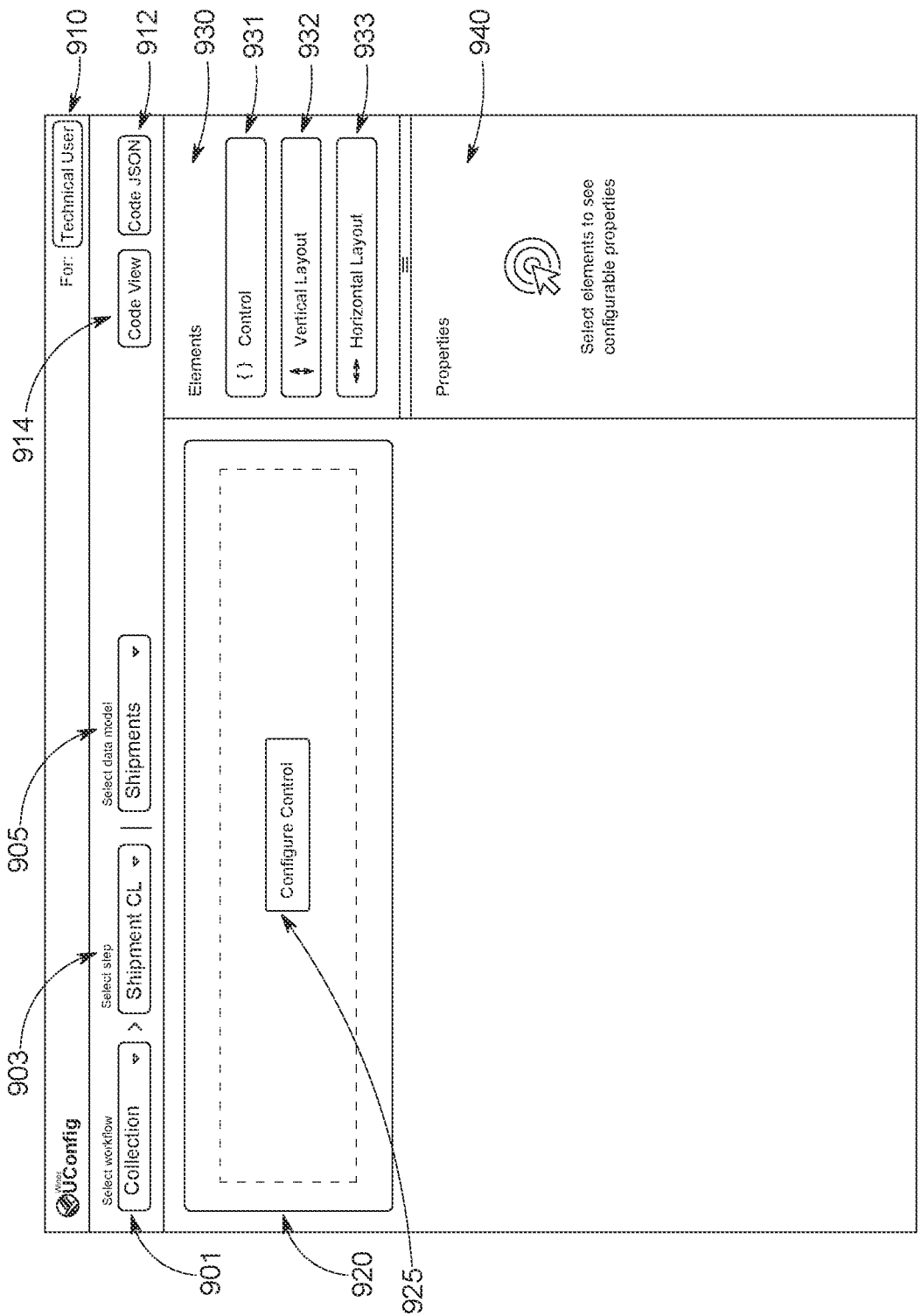

FIG. 9D shows an example GUI for the example UCS, which further illustrates a graphical interface-based configuration in the configuration area 920 from the example in FIG. 9C. Here, the configuration area 920 shows a proposed change to a configure control 925 of the Shipments data model.

Figure 9E:
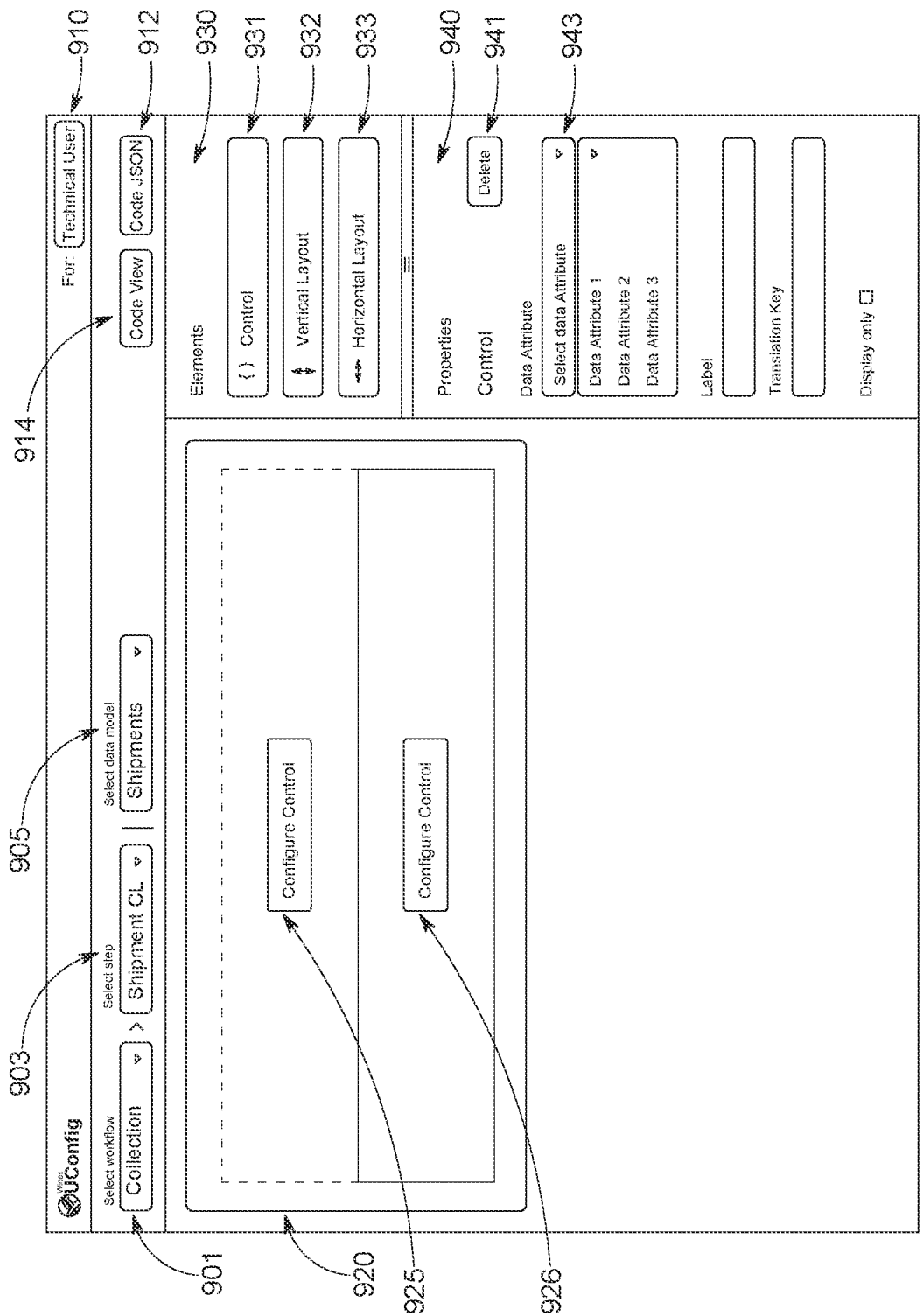

FIG. 9E shows an example GUI for the example UCS, which further illustrates from the example in FIG. 9D, where a second configure control 926 is added to the Shipments data model, and the Properties area 940 shows the properties of this control. In this example, a Data attributes menu 943 (e.g., drop-down menu) is presented, showing selectable attributes for the configure control 926. Also, in this example, the configure control 926 can be deleted by selection of the delete input 941.

Figure 9F:
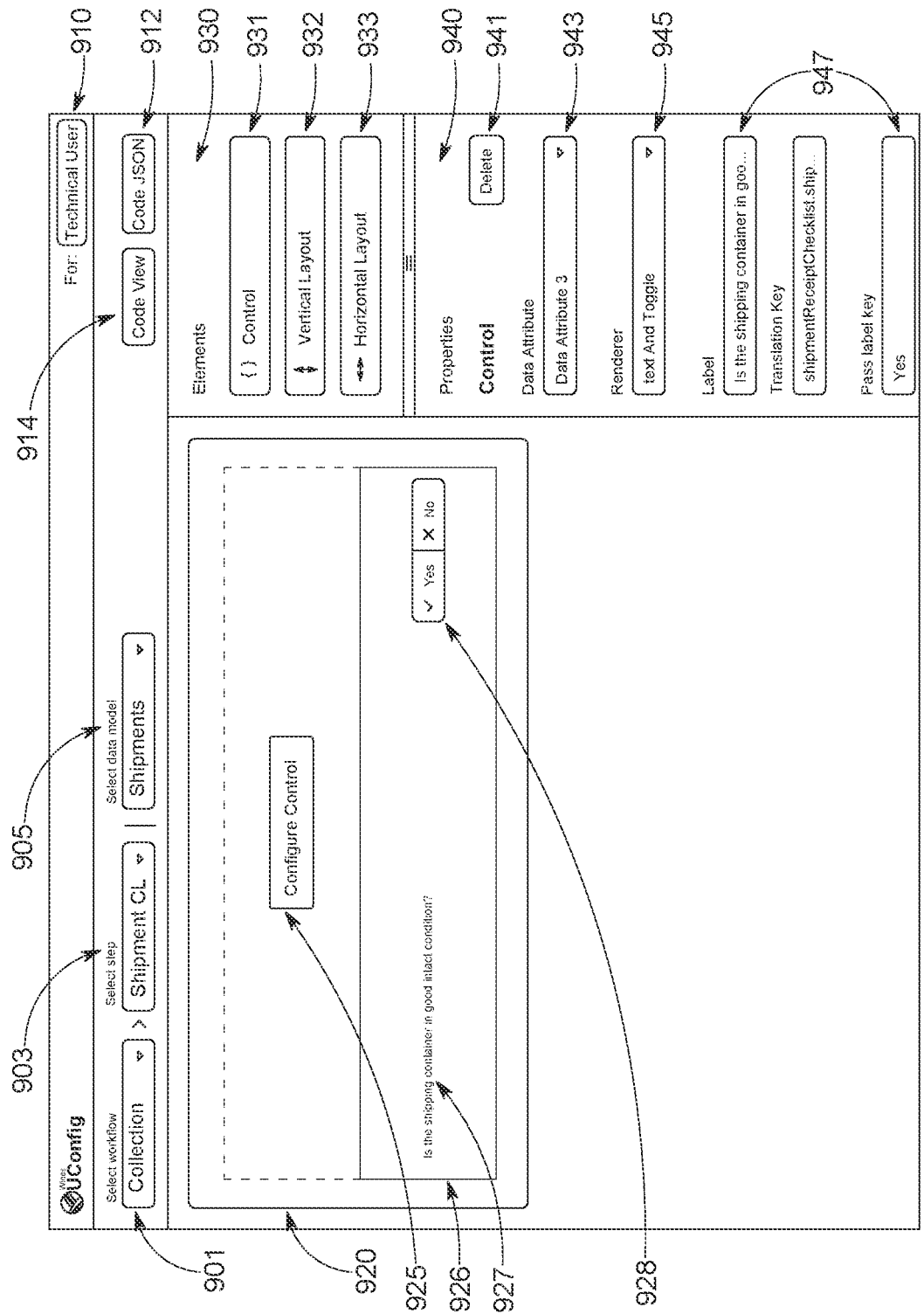

FIG. 9F shows an example GUI for the example UCS, which further illustrates the configuration of the second configuration control 926, where each of the data attributes listed in a data attribute menu 943 can be edited in the Properties area 940. For example, the configure control 926 is configured to present a label 927 (e.g., "Is the shipping container in good intact condition?") when the software application is implemented for the shipments aspect of the supply chain management, in accordance with the Shipments data model. Also configured for the configure control 926 is a pass label 928 (e.g., "Yes" or "No"). The label 927 and pass label 928 can be created by user input in the Properties area 940, e.g., in input boxes 947, based on the type of rendering, e.g., which can be selected in a Renderer menu 945.

Example Computing Devices

Figure 10:
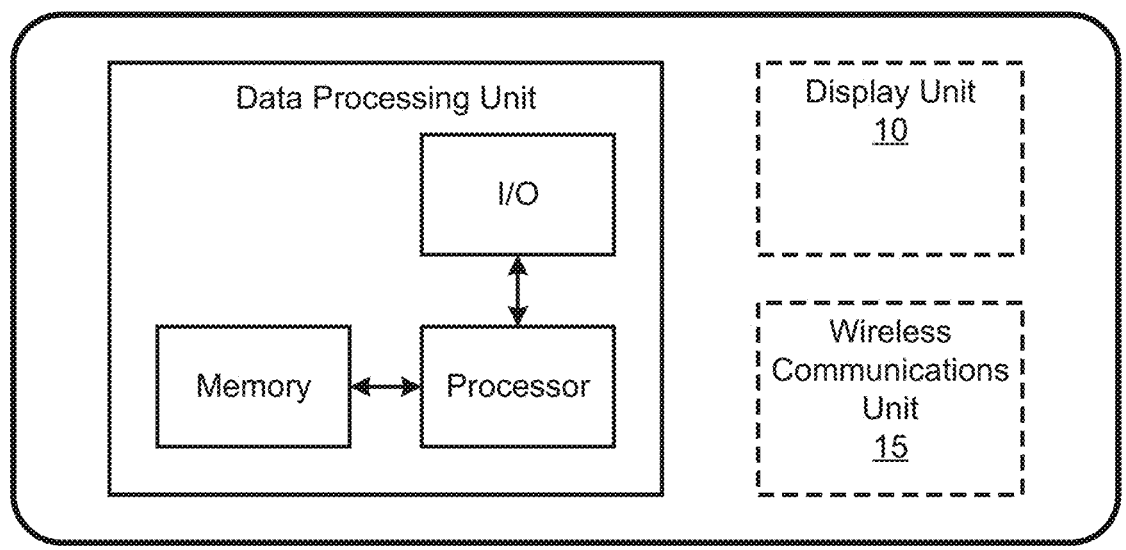
FIG. 10 shows a block diagram of an example embodiment of a computer device.

FIG. 10 shows a block diagram of an example embodiment of a computer device 5 upon which various aspects of the present technology may be implemented. The computer device 5 includes a data processing unit and, optionally, a display unit and/or a wireless communication unit. For example, the computer device 5 can be implemented as a client computer. Also, for example, the computer device 5 can be implemented as a server computer. The data processing unit of the computer device 5 includes one or more processors operable to process data, one or more memories in communication with the processor to store data, and an input/output unit (I/O) to interface the processor and/or memory to other software or hardware modules, units, or devices of the computer device 5 or an external device. For example, the one or more processors can include a central processing unit (CPU), a graphical processing unit (GPU), a microcontroller unit (MCU) or other processor. For example, the one more memories can include and store processor-executable code, which when executed by the processor(s) configures the data processing unit to perform various operations, e.g., such as receiving information, commands, and/or data, processing information and data, and transmitting or providing information/data to another device. In some implementations, the data processing unit can transmit raw or processed data to a computer system or communication network accessible via the Internet (referred to as 'the cloud') that includes one or more remote computational processing devices (e.g., servers in the cloud). To support various functions of the data processing unit, the one or more memories can store information and data, such as instructions, software, values, images, and other data processed or referenced by the processor(s). For example, various types of Random Access Memory (RAM) devices, Read Only Memory (ROM) devices, Flash Memory devices, and other suitable storage media can be used to implement storage functions of the one or more memories. In some embodiments of the computer device 5, for example, the computer device 5 can optionally include a wireless communication unit 15, which can be in data communication with the data processing unit via the I/O. The of the data processing unit can interface the data processing unit to utilize various types of wired or wireless interfaces compatible with typical data communication standards, for example, which can be used in communications of the data processing unit with other devices, via a wireless transmitter/receiver (Tx/Rx) unit, e.g., including, but not limited to, Bluetooth, Bluetooth low energy (BLE), Zigbee, IEEE 802.11, Wireless Local Area Network (WLAN), Wireless Personal Area Network (WPAN), Wireless Wide Area Network (WWAN), WIMAX, IEEE 802.16 (Worldwide Interoperability for Microwave Access (WiMAX)), 3G/4G/LTE/5G cellular communication methods, NFC (Near Field Communication), and parallel interfaces. The I/O of the data processing unit can also interface with other external interfaces, sources of data storage, and/or visual or audio display devices, etc. to retrieve and transfer data and information that can be processed by the processor(s), stored in the memory unit, or exhibited on an output unit of the computer device 5 or an external device. In some embodiments of the computer device 5, for example, the computer device 5 can optionally include a display unit 10 that is in data communication with the data processing unit, e.g., via the I/O, to provide a visual display, an audio display, and/or other sensory display that produces the user interface of the software application in accordance the disclosed technology. In some examples, the display unit 10 can include various types of screen displays, speakers, or printing interfaces, e.g., including but not limited to, light emitting diode (LED), or liquid crystal display (LCD) monitor or screen, cathode ray tube (CRT) as a visual display; audio signal transducer apparatuses as an audio display; and/or toner, liquid inkjet, solid ink, dye sublimation, inkless (e.g., such as thermal or UV) printing apparatuses, etc.

Implementations of the subject matter and the functional operations described in this disclosure can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing unit" or "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

Examples

Several aspects of the present technology are set forth in the following examples. Although several aspects of the present technology are set forth in examples directed to systems, computer-readable mediums, and methods, any of these aspects of the present technology can similarly be set forth in examples directed to any of systems, computer-readable mediums, and methods in other embodiments.

In an example embodiment in accordance with the present technology (example A1), a software configuration service architecture for an enterprise software platform includes a metadata configuration module to store and provide configuration model definitions that define structure and rules of a configuration for the enterprise software platform; a configuration module to process one or more configuration source files and produce a bundled configuration data set; and a configuration deployment module to persist the bundled configuration data set to a data storage of the enterprise software platform; where the configuration module comprises: a first data input to receive the one or more configuration source files associated with a software application executable on one or more client computers, a second data input to receive the configuration model definitions provided by the metadata configuration module, a set of schemas to define data from the one or more configuration source files in accordance with the configuration model definitions, and a configuration build tool to provide a data configuration service, wherein the configuration build tool parses and validates the one or more configuration source files using the configuration model definitions provided by the metadata configuration module to serialize and build the bundled configuration data set.

Example A2 includes the software configuration service architecture of any of examples A1-A9, wherein the configuration module is able to receive the one or more configuration source files from a remote client computer.

Example A3 includes the software configuration service architecture of any of examples A1-A9, further comprising: a configuration management service (CMS) to receive and format the one or more configuration source files from a remote client computer, such that the CMS creates a set of formatted configuration source files to be provided to the configuration module.

Example A4 includes the software configuration service architecture of any of examples A1-A9, wherein the CMS is operable to unify a plurality of different configuration source files and update pathways into a single transaction.

Example A5 includes the software configuration service architecture of any of examples A1 -A9, wherein the configuration model definitions define attribute schema, relationship parameters, and uniqueness constraints.

Example A6 includes the software configuration service architecture of any of examples A1-A9, wherein the configuration deployment module is operable to persist the bundled configuration data set to the data storage of the enterprise software platform by: ingesting the bundled configuration data set; converting a plurality of configuration objects in the bundled configuration data set into a plurality of configuration model objects and a wrapper class for config objects; transforming a list of the plurality of configuration model objects; and storing transforming a list of the plurality of configuration model objects into the data storage of the enterprise software platform.

Example A7 includes the software configuration service architecture of any of examples A1-A9, wherein data storage of the enterprise software platform includes a database.

Example A8 includes the software configuration service architecture of any of examples A1-A9, further comprising: a testing module to evaluate whether the bundled configuration data set to be persisted in the data storage of the enterprise software platform contains all data objects expected in the configuration domain's data schema, after transformations have run.

Example A9 includes the software configuration service architecture of any of examples A1-A8, wherein the metadata configuration module is external to the configuration module.

In an example embodiment in accordance with the present technology (example A10), a system for automating a software application configuration for an enterprise software platform, the system comprising: a database associated with an enterprise software platform, the database resident on one or more computers; a user interface associated with a software application of the enterprise software platform executable on a client computer; at least one processor coupled to the user interface; and a non-transitory memory including processor executable code, wherein the processor executable code upon execution by the at least one processor causes the at least one processor to build a data configuration service for the enterprise software platform, by: receiving one or more configuration source files associated with the software application executable on the client computer; initiating a build process to produce a bundled configuration data set based on the one or more configuration source files; receiving or generating a canonical model of a build data model; receiving or generating a set of configuration model definitions; and building a bundled configuration data set by using (i) a plurality of build inputs based on a source path of the received one or more configuration source files and (ii) the set of configuration model definitions.

Example A11 includes the system of any of examples A10-A12, wherein the configuration model definitions define attribute schema, relationship parameters, and uniqueness constraints.

Example A12 includes the system of example A11 or any of examples A10-A11, wherein the attribute schema describe validations and structure of a configuration entity, and wherein the relationship parameters describe how configuration entities interface.

In an example embodiment in accordance with the present technology (example A13), a method for building a data configuration service for an enterprise software platform, the method comprising: receiving one or more configuration source files associated with a software application executable on one or more client computers; initiating a build process to produce a bundled configuration data set based on the one or more configuration source files; receiving or generating a canonical model of a build data model; receiving or generating a set of configuration model definitions; and building a bundled configuration data set by using (i) a plurality of build inputs based on a source path of the received one or more configuration source files and (ii) the set of configuration model definitions.

Example A14 includes the method of any of examples A13-A17, wherein the building the bundled configuration data set includes parsing the configuration source files, processing the parsed data to perform validation from the set of configuration model definitions, where the validation includes using the set of configuration model definitions to ensure an identity and type of the data models are valid, and inserting validated data model into a configuration store.

Example A15 includes the method of any of examples A13-A17, wherein the configuration model definitions define attribute schema, relationship parameters, and uniqueness constraints.

Example A16 includes the method of example A15 or any of examples A13-A17, wherein the attribute schema describe validations and structure of a configuration entity, and wherein the relationship parameters describe how configuration entities interface.

Example A17 includes the method of any of examples A13-A17, further comprising: initializing a configuration store that maintains settings; and initializing an error reporter to scan and identify for warnings and errors in the configuration store.

In an example embodiment in accordance with the present technology (example B1), a system for automating client-specific software application configuration management for an enterprise software platform includes at least one data store associated with an enterprise software platform, the data store resident on one or more computers; at least one processor coupled to the at least one data store; and a non-transitory memory including processor executable code, wherein the processor executable code upon execution by the at least one processor causes the at least one processor to build a data configuration service for the enterprise software platform, by: receiving data comprising one or more configuration source files associated with a software application of the enterprise software platform executable on a client computer, where the one or more configuration source files includes instructions for a set of configuration changes to a version of the software application executable on the client computer; and processing the received instructions for the set of configuration changes, using: (i) a set of schemas describing at least one of an organization criteria or a validation criteria associated with data structures of the at least one data store and (ii) a set of parameters describing rules governing how to interface with the data structures, to generate an artifact customized for the client computer, wherein the customized artifact comprises a bundle of configuration files configured in a grouped file structure, and wherein the customized artifact is capable of transforming only the version of the software application executable on the client computer in accordance with the instructed set of configuration changes without introducing a change in a master version of the software application of the enterprise software platform executable on one or more other computers.

Example B2 includes the system of any of examples B1-B10, wherein the processing the received instructions for the set of configuration changes comprises: initiating a build process to produce a bundled configuration data set based on the one or more configuration source files; receiving or generating a canonical model of a build data model; receiving or generating a set of configuration model definitions; and building the bundled configuration data set comprising the bundle of configuration files by using (i) a plurality of build inputs based on a source path of the received one or more configuration source files and (ii) the set of configuration model definitions.

Example B3 includes the system of example B2 or any of examples B1-B10, wherein the configuration model definitions define attribute schema, relationship parameters, and uniqueness constraints.

Example B4 includes the system of example B3 or any of examples B1-B10, wherein the attribute schema describe validations and structure of a configuration entity, and wherein the relationship parameters describe how configuration entities interface.

Example B5 includes the system of example B2 or any of examples B1-B10, wherein the building the bundled configuration data set comprises: parsing the one or more configuration source files; processing the parsed data to perform a validation from the set of configuration model definitions, wherein the validation includes using the set of configuration model definitions to ensure an identity and type of the data models are valid, and inserting a validated data model into a configuration store of the non-transitory memory.

Example B6 includes the system of any of examples B1-B10, wherein the processor is configured to use metadata to validate the data represented in the one or more configuration source files, wherein the metadata includes structure and rules of a configuration process.

Example B7 includes the system of any of examples B1-B10, wherein the grouped file structure of the bundle of configuration files includes a serialization of the data represented in the received one or more configuration source files.

Example B8 includes the system of any of examples B1-B10, wherein the processor is configured to break down the artifact based on one or more domains to perform a validation check on one or both of structure of the data in the artifact and content of the data in the artifact.

Example B9 includes the system of any of examples B1-B10, wherein the enterprise software platform is directed to a supply chain management of a personalized medicine treatment comprising a plurality of stakeholder clients selected from a group consisting of a health care provider (HCP), a health care institution, a pharmaceutical manufacturer, a biological material manufacturer, a courier service, and a material storage service, and wherein the system is operable to introduce a new functionality of the supply chain management in the version of the software application of the enterprise software platform executable by the client computer.

Example B10 includes the system of example B9 or any of examples B1-B8, wherein the system is operable to create a new node in the supply chain management of the personalized medicine treatment for a first client computer associated with one of the plurality of stakeholder clients while maintaining an existing version of the supply chain management for a second client computer associated with another of the plurality of stakeholder clients.

In an example embodiment in accordance with the present technology (example B11), a method for automating client-specific software application configuration management for an enterprise software platform includes receiving, at a server in communication with at least one data store operating an enterprise software platform, data comprising one or more configuration source files associated with a software application of the enterprise software platform executable on a client computer, where the one or more configuration source files includes instructions for a set of configuration changes to a version of the software application executable on the client computer; and processing, at the server, the received instructions for the set of configuration change using (i) a set of schemas describing at least one of an organization criteria or a validation criteria associated with data structures of the at least one data store and (ii) a set of parameters describing rules governing how to interface with the data structures, to generate an artifact customized for the client computer, wherein the customized artifact comprises a bundle of configuration files configured in a grouped file structure; and wherein the customized artifact is capable of transforming only the version of the software application executable on the client computer in accordance with the instructed set of configuration changes without introducing a change in a master version of the software application to the enterprise software platform executable on one or more other computers.

Example B12 includes the method of any of examples B11-B20, wherein the processing the received instructions for the set of configuration changes comprises: initiating a build process to produce a bundled configuration data set based on the one or more configuration source files; receiving or generating a canonical model of a build data model; receiving or generating a set of configuration model definitions; and building the bundled configuration data set comprising the bundle of configuration files by using (i) a plurality of build inputs based on a source path of the received one or more configuration source files and (ii) the set of configuration model definitions.

Example B13 includes the method of example B12 or any of examples B11-B20, wherein the configuration model definitions define attribute schema, relationship parameters, and uniqueness constraints.

Example B14 includes the method of example B13 or any of examples B11-B20, wherein the attribute schema describe validations and structure of a configuration entity, and wherein the relationship parameters describe how configuration entities interface.

Example B15 includes the method of example B12 or any of examples B11-B20, wherein the building the bundled configuration data set comprises: parsing the one or more configuration source files; processing the parsed data to perform a validation from the set of configuration model definitions, wherein the validation includes using the set of configuration model definitions to ensure an identity and type of the data models are valid, and inserting a validated data model into a configuration store of the non-transitory memory.

Example B16 includes the method of any of examples B11-B20, comprising at the server, using metadata to validate the data represented in the one or more configuration source files, wherein the metadata includes structure and rules of a configuration process.

Example B17 includes the method of any of examples B11-B20, wherein the grouped file structure of the bundle of configuration files includes a serialization of the data represented in the received one or more configuration source files.

Example B18 includes the method of any of examples B11-B20, comprising: at the server, interrogating the artifact based on one or more domains to perform a validation check on one or both of structure of the data in the artifact and content of the data in the artifact.

Example B19 includes the method of any of examples B11-B20, wherein the enterprise software platform is directed to a supply chain management of a personalized medicine treatment comprising a plurality of stakeholder clients selected from a group consisting of a health care provider (HCP), a health care institution, a pharmaceutical manufacturer, a biological material manufacturer, a courier service, and a material storage service, and wherein implementation of the method by a stakeholder client operating the client computer introduces a new functionality of the supply chain management in the version of the software application of the enterprise software platform executable by the client computer.

Example B20 includes the method of example B19 or any of examples B11-B18, comprising: at the server, creating a new node in the supply chain management of the personalized medicine treatment for the stakeholder client operating the client computer by fulfilling the configuration change to the version of the software application of the enterprise software platform operated by the client computer while maintaining a present version of the supply chain management for another stakeholder client operating a second client computer executing the software application of the enterprise software platform.

Conclusion

From the foregoing, it will be appreciated that specific embodiments of the technology have been described herein for purposes of illustration, but well-known structures and functions have not been shown or described in detail to avoid unnecessarily obscuring the description of the embodiments of the technology. To the extent any materials incorporated herein by reference conflict with the present disclosure, the present disclosure controls. Where the context permits, singular or plural terms can also include the plural or singular term, respectively. Moreover, unless the word "or" is expressly limited to mean only a single item exclusive from the other items in reference to a list of two or more items, then the use of "or" in such a list is to be interpreted as including (a) any single item in the list, (h) all of the items in the list, or (c) any combination of the items in the list. As used herein, the phrase "and/or" as in "A and/or B" refers to A alone, B alone, and both A and B. Where the context permits, singular or plural terms can also include the plural or singular term, respectively. Additionally, the terms "comprising," "including," "having" and "with" are used throughout to mean including at least the recited feature(s) such that any greater number of the same feature and/or additional types of other features are not precluded.

Furthermore, as used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result.

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments can perform steps in a different order. As another example, various components of the technology can be further divided into subcomponents, and/or various components and/or functions of the technology can be combined and/or integrated. Furthermore, although advantages associated with certain embodiments of the technology have been described. in the context of those embodiments, other embodiments can also exhibit such advantages, and not all embodiments need necessarily exhibit such advantages to fall within the scope of the technology.

It should also be noted that other embodiments in addition to those disclosed herein are within the scope of the present technology. For example, embodiments of the present technology can have different configurations, components, and/or procedures in addition to those shown or described herein. Moreover, a person of ordinary skill in the art will understand that these and other embodiments can be without several of the configurations, components, and/or procedures shown or described herein without deviating from the present technology. Accordingly, the disclosure and associated technology can encompass other embodiments not expressly shown or described herein.

What is claimed is:

1. A system for automating client-specific software application configuration management for an enterprise software platform, the system comprising:
   at least one data store associated with an enterprise software platform, the data store resident on one or more computers;
   at least one processor coupled to the at least one data store; and
   a non-transitory memory including processor executable code, wherein the processor executable code upon execution by the at least one processor causes the at least one processor to build a data configuration service for the enterprise software platform, by:
      receiving data comprising one or more configuration source files associated with a software application of the enterprise software platform executable on a client computer,
         where the one or more configuration source files includes instructions for a set of configuration changes to a version of the software application executable on the client computer; and
      processing the received instructions for the set of configuration changes, using: (i) a set of schemas describing at least one of an organization criteria or a validation criteria associated with data structures of the at least one data store and (ii) a set of parameters describing rules governing how to interface with the data structures, to generate an artifact customized for the client computer,
         wherein the artifact customized for the client computer comprises a bundle of configuration files configured in a grouped file structure, and
         wherein the artifact customized for the client computer is capable of transforming only the version of the software application executable on the client computer in accordance with the instructed set of configuration changes without introducing a change in a master version of the software application of the enterprise software platform executable on one or more other computers,
      wherein the processing the received instructions for the set of configuration changes comprises:
         initiating a build process to produce a bundled configuration data set based on the one or more configuration source files;
         receiving or generating a canonical model of a build data model;
         receiving or generating a set of configuration model definitions; and
         building the bundled configuration data set comprising the bundle of configuration files by using (i) a plurality of build inputs based on a source path of the received one or more configuration source files and (ii) the set of configuration model definitions.

2. The system of claim 1 wherein the configuration model definitions define attribute schema, relationship parameters, and uniqueness constraints.

3. The system of claim 2 wherein the attribute schema describe validations and structure of a configuration entity, and wherein the relationship parameters describe how configuration entities interface.

4. The system of claim 1 wherein the building the bundled configuration data set comprises:
  parsing the one or more configuration source files;
  processing the parsed data to perform a validation from the set of configuration model definitions, wherein the validation includes using the set of configuration model definitions to ensure an identity and type of the data models are valid, and
  inserting a validated data model into a configuration store of the non-transitory memory.

5. The system of claim 1 wherein the processor is configured to use metadata to validate the data represented in the one or more configuration source files, wherein the metadata includes structure and rules of a configuration process.

6. The system of claim 1 wherein the grouped file structure of the bundle of configuration files includes a serialization of the data represented in the received one or more configuration source files.

7. The system of claim 1 wherein the processor is configured to break down the artifact based on one or more domains to perform a validation check on one or both of structure of the data in the artifact and content of the data in the artifact.

8. The system of claim 1 wherein the enterprise software platform is directed to a supply chain management of a personalized medicine treatment comprising a plurality of stakeholder clients selected from a group consisting of a health care provider (HCP), a health care institution, a pharmaceutical manufacturer, a biological material manufacturer, a courier service, and a material storage service, and wherein the system is operable to introduce a new functionality of the supply chain management in the version of the software application of the enterprise software platform executable by the client computer.

9. The system of claim 8 wherein the system is operable to create a new node in the supply chain management of the personalized medicine treatment for a first client computer associated with one of the plurality of stakeholder clients while maintaining an existing version of the supply chain management for a second client computer associated with another of the plurality of stakeholder clients.

10. A method for automating client-specific software application configuration management for an enterprise software platform, the method comprising:
  receiving, at a server in communication with at least one data store operating an enterprise software platform, data comprising one or more configuration source files associated with a software application of the enterprise software platform executable on a client computer, where the one or more configuration source files includes instructions for a set of configuration changes to a version of the software application executable on the client computer; and
  processing, at the server, the received instructions for the set of configuration change, using (i) a set of schemas describing at least one of an organization criteria or a validation criteria associated with data structures of the at least one data store and (ii) a set of parameters describing rules governing how to interface with the data structures, to generate an artifact customized for the client computer, wherein the customized artifact comprises a bundle of configuration files configured in a grouped file structure; and
  wherein the customized artifact is capable of transforming only the version of the software application executable on the client computer in accordance with the instructed set of configuration changes without introducing a change in a master version of the software application to the enterprise software platform executable on one or more other computers,
  wherein the processing the received instructions for the set of configuration changes comprises:
    initiating a build process to produce a bundled configuration data set based on the one or more configuration source files;
    receiving or generating a canonical model of a build data model;
    receiving or generating a set of configuration model definitions; and
    building the bundled configuration data set comprising the bundle of configuration files by using (i) a plurality of build inputs based on a source path of the received one or more configuration source files and (ii) the set of configuration model definitions.

11. The method of claim 10 wherein the configuration model definitions define attribute schema, relationship parameters, and uniqueness constraints.

12. The method of claim 11 wherein the attribute schema describe validations and structure of a configuration entity, and wherein the relationship parameters describe how configuration entities interface.

13. The method of claim 10 wherein the building the bundled configuration data set comprises:
  parsing the one or more configuration source files;
  processing the parsed data to perform a validation from the set of configuration model definitions, wherein the validation includes using the set of configuration model definitions to ensure an identity and type of the data models are valid, and
  inserting a validated data model into a configuration store of the non-transitory memory.

14. The method of claim 10, further comprising:
  at the server, using metadata to validate the data represented in the one or more configuration source files, wherein the metadata includes structure and rules of a configuration process.

15. The method of claim 10 wherein the grouped file structure of the bundle of configuration files includes a serialization of the data represented in the received one or more configuration source files.

16. The method of claim 10, further comprising:
  at the server, interrogating the artifact based on one or more domains to perform a validation check on one or both of structure of the data in the artifact and content of the data in the artifact.

17. The method of claim 10 wherein the enterprise software platform is directed to a supply chain management of a personalized medicine treatment comprising a plurality of stakeholder clients selected from a group consisting of a health care provider (HCP), a health care institution, a pharmaceutical manufacturer, a biological material manufacturer, a courier service, and a material storage service, and wherein implementation of the method by a stakeholder client operating the client computer introduces a new functionality of the supply chain management in the version of the software application of the enterprise software platform executable by the client computer.

18. The method of claim 17 comprising:
  at the server, creating a new node in the supply chain management of the personalized medicine treatment for the stakeholder client operating the client computer by fulfilling the configuration change to the version of the software application of the enterprise software platform operated by the client computer while maintaining a present version of the supply chain management for another stakeholder client operating a second client computer executing the software application of the enterprise software platform.

\* \* \* \* \*